(12) United States Patent
Althaus et al.

(10) Patent No.: US 8,105,477 B2
(45) Date of Patent: Jan. 31, 2012

(54) SYSTEM AND METHOD FOR ELECTROCHEMICAL DETECTION OF BIOLOGICAL COMPOUNDS

(75) Inventors: John S. Althaus, Saline, MI (US); Lee Kyonghoon, Ann Arbor, MI (US); Vijay Namasivayam, Ann Arbor, MI (US); Sundaresh N. Brahmasandra, Ann Arbor, MI (US); Kalyan Handique, Ann Arbor, MI (US)

(73) Assignee: Handylab, Inc., Ann Arbor, MI (US)

( * ) Notice: Subject to any disclaimer, the term of this patent is extended or adjusted under 35 U.S.C. 154(b) by 0 days.

(21) Appl. No.: 12/910,112

(22) Filed: Oct. 22, 2010

(65) Prior Publication Data
US 2011/0039345 A1    Feb. 17, 2011

Related U.S. Application Data

(62) Division of application No. 10/553,584, filed as application No. PCT/US2004/011900 on Apr. 16, 2004, now Pat. No. 7,820,030.

(60) Provisional application No. 60/463,047, filed on Apr. 16, 2003.

(51) Int. Cl.
*G01N 27/26* (2006.01)
*G01N 33/53* (2006.01)
*C12Q 1/68* (2006.01)
*C12M 1/34* (2006.01)

(52) U.S. Cl. .......... 205/792; 205/777.5; 205/793.5; 204/450; 204/403.01; 435/6.11; 435/6.12; 435/7.1; 435/287.2; 436/94; 436/86; 436/2; 422/82.01; 422/68.1

(58) Field of Classification Search ..... 204/400–403.15, 204/600, 450; 205/777.5, 775, 787, 792, 205/793.5; 435/6, 6.11, 6.12, 7.1, 287.2; 436/94, 86, 2; 422/68.1, 82.01
See application file for complete search history.

(56) References Cited

U.S. PATENT DOCUMENTS
4,946,952 A    8/1990    Kiefer
(Continued)

FOREIGN PATENT DOCUMENTS
EP    1065278    1/2001

OTHER PUBLICATIONS

Boon, "Electrochemical Sensors Based on DNA-Mediated Charge Transport Chemistry", Thesis submitted to Calif. Inst. Of Tech., Pasadena, CA, Chap. II:27-55, (Aug. 2002).

(Continued)

*Primary Examiner* — Jeffrey T Barton
*Assistant Examiner* — Jennifer Dieterle
(74) *Attorney, Agent, or Firm* — Knobbe, Martens, Olson & Bear, LLP

(57) ABSTRACT

The present invention relates to an electrochemical method for detecting a target polynucleotide. An electrode comprising an electrode surface is provided. The electrode surface includes at least one probe molecule reversibly immobilized with respect to the electrode surface. A first electrochemical signal indicative of an amount of probe molecule immobilized with respect to the electrode surface is obtained. The electrode surface is contacted with a liquid comprising the target polynucleotide. Upon the contacting step, at least some of the probe molecule immobilized with respect to the electrode surface dissociates therefrom. A second electrochemical signal indicative of an amount of probe molecule immobilized with respect to the electrode surface is obtained. The presence of the target polynucleotide is determined at least partially on the basis of the first and second electrochemical signals.

18 Claims, 14 Drawing Sheets

U.S. PATENT DOCUMENTS

| | | |
|---|---|---|
| 5,057,410 A | 10/1991 | Kawasaki et al. |
| 5,075,216 A | 12/1991 | Innis et al. |
| 5,079,351 A | 1/1992 | Sninsky et al. |
| 5,079,352 A | 1/1992 | Gelfand et al. |
| 5,091,310 A | 2/1992 | Innis |
| 5,110,920 A | 5/1992 | Erlich |
| 5,135,627 A | 8/1992 | Soane |
| 5,210,015 A | 5/1993 | Gelfand et al. |
| 5,219,727 A | 6/1993 | Wang et al. |
| 5,232,829 A | 8/1993 | Longiaru et al. |
| 5,278,043 A | 1/1994 | Bannwarth et al. |
| 5,310,652 A | 5/1994 | Gelfand et al. |
| 5,310,893 A | 5/1994 | Erlich et al. |
| 5,312,527 A | 5/1994 | Mikkelsen et al. |
| 5,314,809 A | 5/1994 | Erlich et al. |
| 5,322,770 A | 6/1994 | Gelfand |
| 5,374,553 A | 12/1994 | Gelfand et al. |
| 5,386,022 A | 1/1995 | Sninsky et al. |
| 5,389,512 A | 2/1995 | Kwok et al. |
| 5,389,515 A | 2/1995 | Chmelo et al. |
| 5,405,774 A | 4/1995 | Abramson et al. |
| 5,407,800 A | 4/1995 | Gelfand et al. |
| 5,411,876 A | 5/1995 | Bloch et al. |
| 5,418,149 A | 5/1995 | Gelfand et al. |
| 5,420,029 A | 5/1995 | Gelfand et al. |
| 5,422,242 A | 6/1995 | Young |
| 5,447,839 A | 9/1995 | Manos et al. |
| 5,451,505 A | 9/1995 | Dollinger |
| 5,451,512 A | 9/1995 | Apple et al. |
| 5,455,170 A | 10/1995 | Abramson et al. |
| 5,464,945 A | 11/1995 | Reynolds et al. |
| 5,466,591 A | 11/1995 | Abramson et al. |
| 5,468,613 A | 11/1995 | Erlich et al. |
| 5,487,972 A | 1/1996 | Gelfand et al. |
| 5,491,063 A | 2/1996 | Fisher et al. |
| 5,491,086 A | 2/1996 | Gelfand et al. |
| 5,491,225 A | 2/1996 | Picone et al. |
| 5,501,963 A | 3/1996 | Burckhardt |
| 5,508,168 A | 4/1996 | Orle et al. |
| 5,512,462 A | 4/1996 | Cheng |
| 5,527,669 A | 6/1996 | Resnick et al. |
| 5,527,898 A | 6/1996 | Bauer et al. |
| 5,538,848 A | 7/1996 | Livak et al. |
| 5,543,296 A | 8/1996 | Sobol et al. |
| 5,550,039 A | 8/1996 | Trachtenberg |
| 5,550,040 A | 8/1996 | Purohit et al. |
| 5,561,058 A | 10/1996 | Gelfand et al. |
| 5,565,339 A | 10/1996 | Bloch et al. |
| 5,567,809 A | 10/1996 | Apple et al. |
| 5,571,673 A | 11/1996 | Picone |
| 5,573,906 A | 11/1996 | Bannwarth et al. |
| 5,593,836 A | 1/1997 | Niemiec et al. |
| 5,599,662 A | 2/1997 | Respess |
| 5,618,711 A | 4/1997 | Gelfand et al. |
| 5,635,348 A | 6/1997 | Leong |
| 5,639,871 A | 6/1997 | Bauer et al. |
| 5,641,864 A | 6/1997 | Gelfand |
| 5,643,723 A | 7/1997 | Persing et al. |
| 5,643,724 A | 7/1997 | Fildes et al. |
| 5,648,482 A | 7/1997 | Meyer |
| 5,665,548 A | 9/1997 | Erlich et al. |
| 5,665,551 A | 9/1997 | Gelfand et al. |
| 5,693,517 A | 12/1997 | Gelfand et al. |
| 5,705,627 A | 1/1998 | Manos et al. |
| 5,763,184 A | 6/1998 | Reynolds et al. |
| 5,804,375 A | 9/1998 | Gelfand et al. |
| 5,804,436 A | 9/1998 | Okun et al. |
| 5,837,442 A | 11/1998 | Tsang |
| 5,869,244 A | 2/1999 | Martin et al. |
| 5,908,743 A | 6/1999 | Christopherson et al. |
| 5,912,117 A | 6/1999 | Dodge et al. |
| 5,919,646 A | 7/1999 | Okun et al. |
| 5,939,292 A | 8/1999 | Gelfand et al. |
| 5,952,202 A | 9/1999 | Aoyagi et al. |
| 5,968,745 A | 10/1999 | Thorp et al. |
| 5,968,799 A | 10/1999 | Gelfand et al. |
| 5,994,056 A | 11/1999 | Higuchi |
| 6,001,611 A | 12/1999 | Will |
| 6,010,607 A | 1/2000 | Ramsey |
| 6,074,827 A | 6/2000 | Nelson et al. |
| 6,090,557 A | 7/2000 | Weiss |
| 6,096,509 A | 8/2000 | Okun et al. |
| 6,100,541 A | 8/2000 | Nagle et al. |
| 6,103,537 A | 8/2000 | Ullman et al. |
| 6,120,666 A | 9/2000 | Jacobson et al. |
| 6,132,580 A | 10/2000 | Mathies et al. |
| 6,171,785 B1 | 1/2001 | Higuchi |
| 6,174,670 B1 | 1/2001 | Wittwer et al. |
| 6,194,561 B1 | 2/2001 | Erlich et al. |
| 6,214,979 B1 | 4/2001 | Gelfand et al. |
| 6,235,471 B1 | 5/2001 | Knapp et al. |
| 6,280,967 B1 | 8/2001 | Ransom et al. |
| 6,287,774 B1 | 9/2001 | Kikiforov |
| 6,346,379 B1 | 2/2002 | Gelfand et al. |
| 6,353,475 B1 | 3/2002 | Jensen et al. |
| 6,358,387 B1 | 3/2002 | Kopf-sill et al. |
| 6,365,375 B1 | 4/2002 | Dietmaier et al. |
| 6,366,924 B1 | 4/2002 | Parce |
| 6,379,884 B2 | 4/2002 | Wada et al. |
| 6,399,320 B1 | 6/2002 | Markau et al. |
| 6,399,952 B1 | 6/2002 | Majer et al. |
| 6,403,786 B1 | 6/2002 | Muhlegger et al. |
| 6,420,143 B1 | 7/2002 | Kopf-Sill |
| 6,430,512 B1 | 8/2002 | Gallagher |
| 6,447,724 B1 | 9/2002 | Jensen et al. |
| 6,465,257 B1 | 10/2002 | Parce et al. |
| 6,468,761 B2 | 10/2002 | Yang et al. |
| 6,468,763 B1 | 10/2002 | Farinas |
| 6,472,141 B2 | 10/2002 | Nikiforov |
| 6,475,364 B1 | 11/2002 | Dubrow et al. |
| 6,498,005 B1 | 12/2002 | Nikiforov et al. |
| 6,498,497 B1 | 12/2002 | Chow et al. |
| 6,506,609 B1 | 1/2003 | Wada et al. |
| 6,509,157 B1 | 1/2003 | Martinez |
| 6,556,923 B2 | 4/2003 | Gallagher et al. |
| 6,558,916 B2 | 5/2003 | Veerapandian et al. |
| 6,558,945 B1 | 5/2003 | Kao |
| 6,589,729 B2 | 7/2003 | Chan et al. |
| 6,592,821 B1 | 7/2003 | Wada et al. |
| 6,613,211 B1 | 9/2003 | McCormick et al. |
| 6,613,513 B1 | 9/2003 | Parce et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,632,655 B1 | 10/2003 | Mehta et al. |
| 6,649,358 B1 | 11/2003 | Parce et al. |
| 6,681,616 B2 | 1/2004 | Spaid et al. |
| 6,685,813 B2 | 2/2004 | Williams et al. |
| 6,695,009 B2 | 2/2004 | Chien et al. |
| 6,733,645 B1 | 5/2004 | Chow |
| 6,740,518 B1 | 5/2004 | Duong et al. |
| 6,750,661 B2 | 6/2004 | Brooks et al. |
| 6,777,184 B2 | 8/2004 | Nikiforov et al. |
| 6,787,015 B2 | 9/2004 | Lackritz et al. |
| 6,787,016 B2 | 9/2004 | Tan et al. |
| 6,801,875 B1 | 10/2004 | Wolk et al. |
| 6,838,680 B2 | 1/2005 | Maher et al. |
| 6,858,185 B1 | 2/2005 | Kopf-sill et al. |
| 6,900,889 B2 | 5/2005 | Bjornson et al. |
| 6,905,583 B2 | 6/2005 | Wainright et al. |
| 6,939,451 B2 | 9/2005 | Zhao et al. |
| 7,037,416 B2 | 5/2006 | Parce et al. |
| 7,039,527 B2 | 5/2006 | Tripathi et al. |
| 7,040,144 B2 | 5/2006 | Spaid et al. |
| 7,060,171 B1 | 6/2006 | Nikiforov et al. |
| 7,099,778 B2 | 8/2006 | Chien |
| 7,105,304 B1 | 9/2006 | Nikiforov et al. |
| 7,161,356 B1 | 1/2007 | Chien |
| 7,169,277 B2 | 1/2007 | Ausserer et al. |
| 7,276,330 B2 | 10/2007 | Chow et al. |
| 7,419,784 B2 | 9/2008 | Dubrow et al. |
| 7,494,577 B2 | 2/2009 | Williams et al. |
| 7,521,186 B2 | 4/2009 | Burd Mehta |
| 7,595,197 B2 | 9/2009 | Brasseur |
| 7,670,559 B2 | 3/2010 | Chien et al. |
| 7,723,123 B1 | 5/2010 | Murphy et al. |
| 2002/0155477 A1 | 10/2002 | Ito |

| | | |
|---|---|---|
| 2005/0121324 A1 | 6/2005 | Park et al. |
| 2005/0133370 A1 | 6/2005 | Park et al. |
| 2005/0170362 A1 | 8/2005 | Wada et al. |
| 2005/0202470 A1 | 9/2005 | Sundberg et al. |
| 2006/0113190 A1 | 6/2006 | Kurnik |
| 2006/0246493 A1 | 11/2006 | Jensen et al. |
| 2006/0246533 A1 | 11/2006 | Fathollahi et al. |
| 2007/0026421 A1 | 2/2007 | Sundberg et al. |

OTHER PUBLICATIONS

Cho et al., "Fabrication of a Multi-Electrode Array DNA Sensor for Electrochemical Genotyping", Journal of the Korean Physical Society, 41(6):1054-1057, (Dec. 2002).

De-los-Santos Alvarez et al., "New Scheme for Electrochemical Detection of DNA Based on Electrocatalytic Oxidation of NADH", Electrochemistry Communications, 5:267-271, (2003).

Dequaire et al., "Screen Printing of Nucleic Acid Detecting Carbon Electrodes", Anal. Chem., 74:4370-4377, (2002).

Gooding, "Electrochemical DNA Hybridization Biosensors", Electroanalysis, vol. 14, issue 17, pp. 1149-1156, (2002).

Mascini et al., "DNA electrochemical biosensors", Fresenius J. Anal. Chem., 369: 15-22, (2001).

Piedade et al., "Electrochemical Sensing of DNA-Adriamycin Interactions", Bioelectrochemistry, 56:81-83, (2002).

Plambeck et al., "Electrochemical Studies of Antitumor Antibiotics", J. Electrochem Soc.: Electrochemical Science and Technology, pp. 2556-2563, (Dec. 1984).

Popovich, "Mediated Electrochemical Detection of Nucleic Acids Discovery and Clinical Diagnosis", Med. Devicelink archive, pp. 1-8 (Apr. 1, 2003).

Wang, "Nanoparticle-based electrochemical DNA detection", Analytica Chimica Acta 500, pp. 247-257, (2003).

Wang, "Survey and Summary, from DNA Biosensors to Gene Chips", Nucleic Acids Research, 28(16):3011-3016, (2000).

Zhang et al., "Carbon Paste Electrode Based on Surface Activation for Trace Adriamycin Determination by a Preconcentration and Voltammetric Method"—Analytical Sciences, 18:1089-1092, (Oct. 2002).

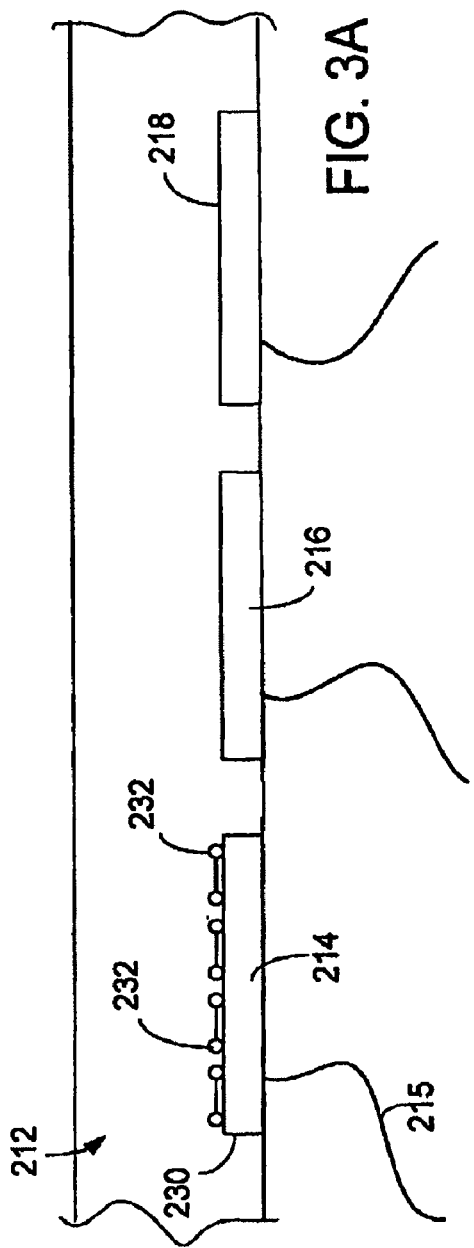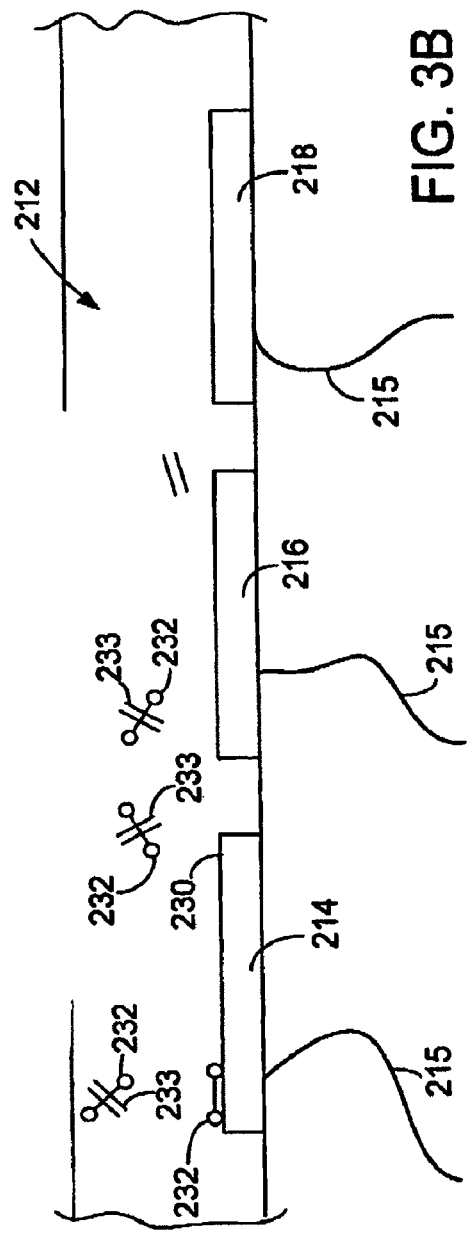

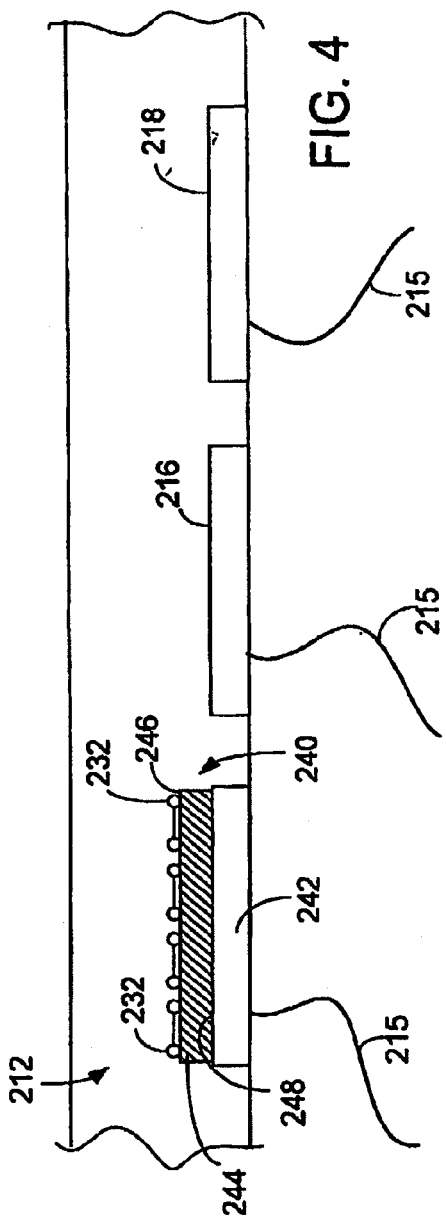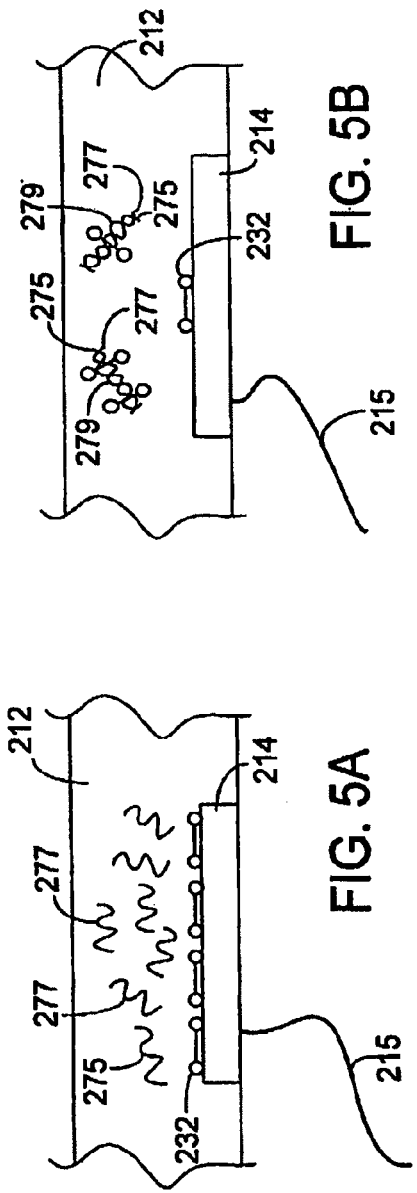

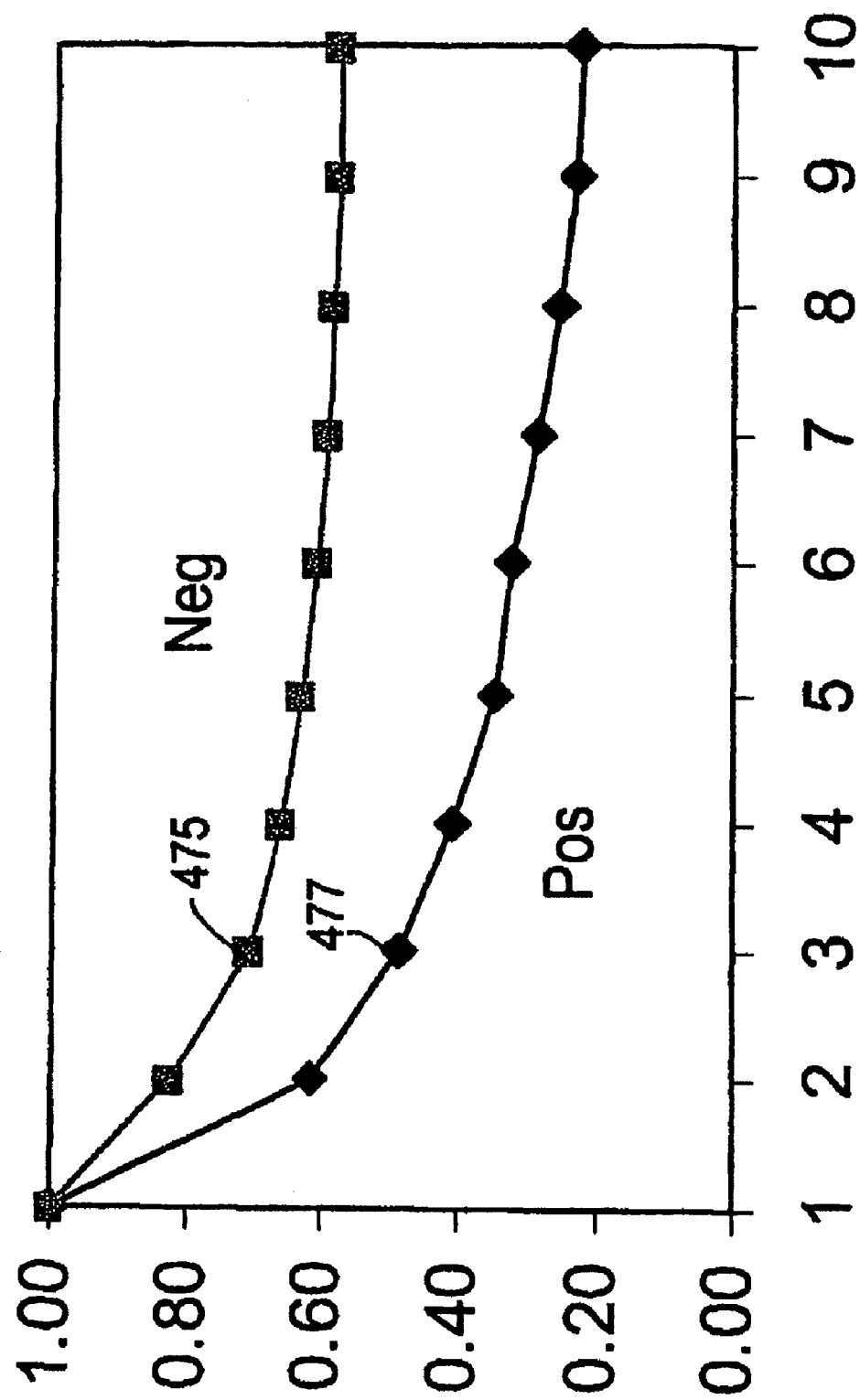

SYSTEM AND METHOD FOR ELECTROCHEMICAL DETECTION OF BIOLOGICAL COMPOUNDS

CLAIM OF PRIORITY

This application is a divisional of, and claims priority under 35 U.S.C. §121 to U.S. patent application Ser. No. 10/553,584, filed Oct. 17, 2005, which is the U.S. National Phase Application under 35 U.S.C. §371 of International Application No. PCT/US2004/11900, filed Apr. 16, 2004, and claims the benefit of priority under 35 U.S.C. §119 to U.S. Provisional Patent Application No. 60/463,047, filed Apr. 16, 2003, which applications are incorporated herein by reference in their entirety.

FIELD OF THE INVENTION

The present invention relates to electrochemical detection of biological compounds, such as polynucleotides, proteins, and viruses.

BACKGROUND OF THE INVENTION

The analysis of a biological sample often includes detecting one or more compounds, e.g., polynucleotides and/or proteins present in the sample. One example of detection is qualitative detection, which relates to, e.g., the determination of the presence of a polynucleotide and/or the determination of information related to, e.g., the type, size, presence or absence of mutations, and/or the sequence of the polynucleotide. Another example of detection is quantitative detection, which relates to, e.g., the determination of the amount of polynucleotide present. Detection may include both qualitative and quantitative aspects.

Compounds including polynucleotides and proteins may be detected electrochemically without the need for light sources.

SUMMARY OF THE INVENTION

A first aspect of the invention relates to an electrochemical method for detecting a target compound, which may be a polynucleotide. A first electrochemical signal is obtained. The first electrochemical signal may comprise a portion arising from a first amount of a probe molecule that is not intercalated with the target polynucleotide. An amount of target polynucleotide in fluid communication with the first amount of probe molecule is modified. A second electrochemical signal comprising a portion arising from a second amount of probe molecule not intercalated with the target polynucleotide is obtained. The presence of the target polynucleotide may be determined based on the first and second electrochemical signals.

Modifying the amount of target polynucleotide may comprise subjecting the target polynucleotide to at least one amplification cycle. An electrode may be used to obtain the first and second electrochemical signals. The polynucleotide may be subjected to the at least one amplification cycle in the presence of the electrode.

Upon modifying an amount of target polynucleotide, a portion Δ of the first amount of probe molecule may intercalate with the target polynucleotide. The second electrochemical signal may be different from the first electrochemical signal by an amount indicative of Δ.

The first and second electrochemical signals may be substantially free of an electrochemical signal from intercalated probe molecule. The probe molecule may be substantially free of polynucleotides having a length of at least 4 bases, e.g., 8 bases.

One or both of the first and second electrochemical signals may arise from an electrochemically active moiety of the probe molecule that is free of purines.

In some embodiments, the probe molecule may comprise at least two cyclic groups. The probe molecule may include at least three 6-membered rings. The probe molecule may be an anthracycline, methylene blue, or derivative thereof, e.g., the probe molecule may be selected from the group consisting of daunomycin, doxorubicin, methylene blue, toluidine blue O, azure A, azure B, azure C, thionin, and derivatives thereof.

Where an electrode is used to obtain the first and second electrochemical signals, the electrode may be substantially free of molecules covalently bound to the electrode surface via linking groups comprising alkyl chains at least 5 carbon atoms long. In some embodiments, the electrode is free of covalently bound molecules configured to associate with the target compound.

The probe molecule may comprise (a) a polynucleotide having a sequence sufficiently complementary to a sequence of the target polynucleotide to form a duplex therewith and (b) an electrochemically active moiety that is free of purines, the first and second electrochemical signals arising from the electrochemically active moiety.

The electrochemical method may further comprise detecting a second polynucleotide. A third electrochemical signal comprising a portion arising from a first amount of a second probe molecule not intercalated with the target polynucleotide or the second target polynucleotide is obtained. The second probe molecule comprises (a) a polynucleotide having a sequence sufficiently complementary to a sequence of the second target polynucleotide to form a duplex therewith and different from a polynucleotide sequence of a polynucleotide of the probe molecule and (b) an electrochemically active moiety that is free of purines. An amount of the second target polynucleotide in fluid communication with the first amount of the second probe molecule is modified. A second electrochemical signal comprising a portion arising from a second amount of the second probe molecule not intercalated with either the target polynucleotide or the second polynucleotide is obtained.

The first and second electrochemical signals may be obtained using an electrode and the second electrochemical signal may be obtained without contacting the electrode with fresh probe molecule intermediate obtaining the first and second electrochemical signals.

The second electrochemical signal may be substantially free of a portion arising from an oxidation or reduction of guanine residues, if present, of the target polynucleotide.

The first and second electrochemical signals may arise from the application of a potential difference between a working electrode and a reference electrode. The potential difference may be between −1.2 V and 0 V as against a Ag/AgCl reference electrode.

The first and second electrochemical signals may arise from a reduction of an electrochemically active moiety of the probe molecule.

In some embodiments, a first electrochemical signal from a first amount of a probe molecule is obtained. The probe molecule has a first electrochemical activity when not intercalated with the target polynucleotide and a second, different electrochemical activity when intercalated with the target polynucleotide. An amount of target polynucleotide in fluid communication with the first amount of probe molecule is modified whereupon a portion Δ of the first amount of probe molecule intercalates with the target polynucleotide. A second electrochemical signal is obtained from a second amount of probe molecule.

The second electrochemical activity may be lower than the first electrochemical activity. The second electrochemical signal may be different from the first electrochemical signal by an amount indicative of $\Delta$.

In some embodiments, a first electrochemical signal is obtained from a first amount of a probe molecule reversibly immobilized with respect to an electrode. An amount of target polynucleotide in fluid communication with the first amount of probe molecule is modified. A second electrochemical signal is obtained from a second amount of the probe molecule reversibly immobilized with respect to the electrode.

In some embodiments, an electrode is used to obtain a first electrochemical signal, the first electrochemical signal being indicative of a first amount of probe molecule and arising from a polynucleotide-free electrochemically active moiety of the probe molecule. The electrode is used to obtain a second electrochemical signal, the second electrochemical signal is indicative of a second amount of probe molecule and arises from the polynucleotide-free electrochemically active moiety of the probe molecule.

An amount of target polynucleotide in fluid communication with the electrode may be modified intermediate obtaining the first and second electrochemical signals.

Prior to using the electrode to obtain the first electrochemical signal and with the electrode (a) dry and (b) having an amount of probe molecule associated therewith, the electrode may be contacted with a liquid, e.g., water or an aqueous solution. Prior to contacting the electrode with the liquid, the electrode may be substantially free of the target polynucleotide.

Prior to using the electrode to obtain the second electrochemical signal and with the electrode (a) substantially free of the target polynucleotide and (b) having an amount of probe molecule associated therewith, the electrode may be contacted with a liquid comprising the target polynucleotide. Prior to contacting the electrode with the liquid, the electrode may be substantially free of polynucleotides having sequences that are (a) at least 4 bases in length, e.g., at least 8 bases in length and (b) sufficiently complementary to a sequence of the target polynucleotide to form a duplex therewith. Prior to contacting the electrode with a liquid, the electrode may be dry.

One or both of the first and second amounts of probe molecule may be non-intercalated with the target polynucleotide.

At some time prior to using the electrode to obtain the first electrochemical signal, the electrode (a) may have an amount of probe molecule associated therewith and (b) may be substantially free of polynucleotides having sequences that are (a) at least 4 bases, e.g., at least 8 bases in length and (b) sufficiently complementary to a sequence of the target polynucleotide to form a duplex therewith. At the some time prior, the electrode may be dry.

The electrode may be substantially free of liquid mercury.

Substantially all of the first amount of probe molecule and substantially all of the second amount of probe molecule may be immobilized with respect to the electrode.

Modifying the amount of target polynucleotide in fluid communication with the electrode may comprise increasing the amount of target polynucleotide in fluid communication with the electrode and a magnitude of the second electrochemical signal may be less than a magnitude of the first electrochemical signal.

The electrode may comprise a cationic surfactant.

A difference between the first and second amounts of target polynucleotide may be less than $5 \times 10^{-9}$ molar, e.g., less than $1 \times 10^{-9}$ molar, e.g., $0.5 \times 10^{-9}$ molar.

Modifying the amount of polynucleotide in fluid communication with the electrode may comprise increasing the amount of polynucleotide in fluid communication from zero to a non-zero amount.

In some embodiments, a first electrochemical signal is obtained from a first amount of probe molecule in the presence of a first polynucleotide and a second polynucleotide, the first and second polynucleotides may be sufficiently complementary to form a duplex. The first and second polynucleotides are subjected to at least one of an annealing step or a melting step in the presence of the first amount of probe molecule. Then, a second electrochemical signal is obtained from the probe molecule.

The first electrochemical signal may be obtained at a temperature below the melting point of the duplex region and the second electrochemical signal may be obtained at a temperature at least as great as the melting point of the duplex.

Subjecting the first and second polynucleotides to at least one of an annealing step or a melting step may further comprise subjecting the first and second polynucleotides to at least one amplification step intermediate obtaining the first and second electrochemical signals and in the presence of the probe molecule.

The first electrochemical signal may be obtained using an electrode and the method may comprise contacting the electrode with a liquid prior to obtaining the first electrochemical signal. The electrode may be dry prior to being contacted with the liquid.

The first electrochemical signal may be obtained using an electrode and the method may comprise contacting the electrode with a liquid prior to obtaining the first electrochemical signal. Prior to the contacting step, the electrode may comprise at least a portion of the first amount of probe molecule reversibly immobilized with respect thereto.

Another aspect of the invention relates to a method for preparing a device for electrochemically determining the presence of a polynucleotide. An electrode is contacted with a liquid comprising an intercalating compound. The intercalating compound has a first electrochemical activity when not intercalated with a double stranded polynucleotide and a second, different electrochemical activity when intercalated with a double stranded polynucleotide. In some embodiments, liquid is removed from the electrode. The electrode may be dried.

Prior to drying the electrode, the method may omit binding polynucleotide sequences having a length of greater than 4 bases, e.g., greater than 8 bases the electrode.

The electrode may be used to prepare a microfluidic device comprising the electrode.

After drying the electrode, the electrode may be enclosed within an enclosure, which may be hermetic. The hermetic enclosure may limit or prevent the passage of gas therethrough. The enclosure may comprise a flexible metal foil and/or a polymer film.

Another aspect of the invention relates to a method for preparing an electrode. A flowable mixture is prepared. The mixture comprises a plurality of conductive particles and a probe molecule. The conductive particles may be carbon. The mixture may include a filler. The mixture may include a polymer.

Another aspect of the invention relates to a method for preparing a device for electrochemically determining the presence of a polynucleotide. An electrode is contacted with a liquid comprising an intercalating compound, the intercalating compound having a first electrochemical activity when not intercalated with a double stranded polynucleotide and a second, different electrochemical activity when intercalated with a double stranded polynucleotide. The microfluidic device is sealed within an enclosure, which may be hermetic.

Another aspect of the invention relates to an electrode comprising, a reversibly immobilized electrochemically active intercalating compound. The electrode is free of liquid. For example, the electrode may be dry. The electrode may be sealed within an enclosure, which may be hermetic.

Another aspect of the invention relates to an electrochemical method for detecting a target polynucleotide. The method comprises contacting an electrode with a liquid, the electrode comprising an amount of probe molecule immobilized with respect to the electrode, the electrode, prior to contact with the liquid, being substantially free of the target polynucleotide. A first electrochemical signal indicative of an amount of probe molecule immobilized with respect to an electrode is obtained. After obtaining the first electrochemical signal, an amount of target polynucleotide in contact with the electrode is modified. Then, a second electrochemical signal indicative of the amount of probe molecule immobilized with respect to the electrode is obtained.

In some embodiments, a first electrochemical signal is obtained using an electrode, the electrode comprising an electrode surface, the electrode surface comprising at least one probe molecule reversibly immobilized with respect to the electrode surface, the first electrochemical signal arising from the probe molecule and indicative of an amount of the probe molecule immobilized with respect to the electrode surface. The electrode surface is contacted with a liquid comprising the target polynucleotide. A second electrochemical signal indicative of an amount of probe molecule immobilized with respect to the electrode surface is obtained. The presence of the target polynucleotide is determined based on the first and second electrochemical signals.

In some embodiments, the method comprises providing a reference electrode, the reference electrode comprising a reference electrode surface, wherein the first electrochemical signal may be a reference electrochemical signal obtained using the reference electrode surface of the reference electrode. The reference electrochemical signal may be obtained simultaneously with or after the second electrochemical signal.

The probe molecule may be a metal perchlorate and may comprise at least one of tris(2,2'-bipyridyl)cobalt(III) perchlorate and tris(1,10-phenanthroline)cobalt(III) perchlorate.

In some embodiments, an electrode having an electrode surface is provided. The electrode surface comprises at least one probe molecule in electrochemical communication therewith, whereby the electrode may be used to obtain an electrochemical signal indicative of an amount of the probe molecule in electrochemical communication with the electrode surface. A first electrochemical signal indicative of an amount of probe molecule in electrochemical communication with the electrode surface is obtained. The electrode surface is contacted with a liquid comprising the target polynucleotide, whereupon at least some of the probe molecule in electrochemical communication with the electrode surface associates with the target polynucleotide, wherein probe molecule associated with the target polynucleotide has a reduced electrochemical communication with the electrode surface compared to probe molecule not associated with the target polynucleotide. A second electrochemical signal indicative of an amount of probe molecule in electrochemical communication with the electrode surface is obtained. The presence of the target polynucleotide is determined based on the first and second electrochemical signals.

In some embodiments, an electrode having an electrode surface is provided. The electrode surface comprises at least one probe molecule reversibly immobilized with respect to the electrode surface. The electrode surface is contacted with a liquid comprising (a) the target polynucleotide and (b) a complementary polynucleotide that is sufficiently complementary to the target polynucleotide to form at least one duplex region therewith. A first electrochemical signal indicative of an amount of probe molecule immobilized with respect to the electrode surface is obtained. After the step of contacting the electrode surface with the liquid, the target polynucleotide and complementary polynucleotide are subjected to at least one annealing step, wherein the target polynucleotide and complementary polynucleotide anneal to form the at least one duplex region. After subjecting the target polynucleotide and complementary polynucleotide to annealing, a second electrochemical signal indicative of an amount of probe molecule immobilized with respect to the electrode surface is obtained. The presence of the target polynucleotide is determined based on the first and second electrochemical signals.

In some embodiments, an electrochemical detection chamber comprising an electrode is provided. The electrode comprising an electrode surface having an associated probe molecule. At least: (a) a first target polynucleotide and (b) a first complementary polynucleotide are introduced to the detection chamber. The first target polynucleotide and the first complementary polynucleotide are sufficiently complementary to one another to form a first duplex. When the first probe molecule is (i) in the presence of the first target polynucleotide and the first complementary polynucleotide, and (ii) at a temperature below a melting point of the first duplex, the first probe molecule comprises a first electrochemical activity with respect to the electrode surface, and, when the first probe molecule is (i) in the presence of the first target polynucleotide and the first complementary polynucleotide and (ii) at a temperature above a melting point of the first duplex, the first probe molecule comprises a second, different electrochemical activity with respect to the electrode surface.

A first electrochemical signal indicative of the electrochemical activity of the first probe molecule is obtained, the first electrochemical signal being obtained with the first target polynucleotide and the first complementary polynucleotide at a first temperature;

After obtaining the first electrochemical signal, if the first temperature was less than the melting point of the first duplex, the temperature of the first duplex is increased to a temperature greater than the melting point of the first duplex, if the first temperature was greater than the melting point of the first duplex, the temperature of the first target polynucleotide and the first complementary polynucleotide is decreased to a temperature less than the melting point of the first duplex. Then, a second electrochemical signal indicative of an electrochemical activity of the first probe molecule is obtained. The presence of the first target polynucleotide based on the first and second electrochemical signals.

Another aspect of the invention relates to an electrochemical method for detecting at least first and second target polynucleotides in a mixture. The method comprises providing an electrode comprising an electrode surface, the electrode surface comprising at least first and second probe molecules reversibly immobilized with respect to the electrode surface, wherein each of the first and second probe molecules comprises (a) a respective electrochemically active portion comprising a respective, different oxidation-reduction potential and (b) a respective, different polynucleotide, the polynucleotide of the first probe molecule being complementary to at least a portion of the first target polynucleotide and the polynucleotide of the second probe molecule being complementary to at least a portion of the second target polynucleotide. A first electrochemical signal indicative of a respective amount of the first probe molecule reversibly immobilized with respect to the electrode surface is obtained. A second electrochemical signal indicative of a respective amount of the second probe molecule reversibly immobilized with respect to the electrode surface is obtained. The electrode surface is contacted with a liquid comprising at least one of the first and second target polynucleotides, whereupon (a) if the first target polynucleotide is present, at least some of the first probe molecule immobilized with respect to the electrode surface dissociates therefrom and the polynucleotide of the first probe molecule hybridizes with the first target polynucleotide and (b) if the second polynucleotide is present, at least some of the second probe molecule immobilized with respect to the electrode surface dissociates therefrom and the polynucleotide of the second probe molecule hybridizes with the second target polynucleotide. After contacting the electrode surface with the liquid, obtaining a third electrochemical signal indicative of an amount of the first probe molecule immobilized with respect to the electrode surface. After contacting the electrode surface with the liquid, obtaining a fourth electrochemical signal indicative of an amount of the second probe molecule immobilized with respect to the electrode surface. The presence of the first target polynucleotide based on the first and third electrochemical signals. The presence of the second target polynucleotide is determined based on the second and fourth electrochemical signals.

Another aspect of the invention relates to a method for detecting an antigen or an antibody. An electrode comprising an electrode surface is provided. The electrode surface comprises at least one probe molecule reversibly immobilized with respect to the electrode surface, the probe molecule comprising an antibody to the antigen or an antigen to the antibody. A first electrochemical signal indicative of an amount of probe molecule immobilized with respect to the electrode surface is obtained. The electrode surface is contacted with a liquid comprising the antigen (or the antibody), whereupon at least some of the probe molecule immobilized with respect to the electrode surface dissociates therefrom. A second electrochemical signal indicative of an amount of probe molecule immobilized with respect to the electrode surface is obtained. The presence of the antigen or antibody is determined based on the first and second electrochemical signals.

Another aspect of the invention relates to a manufacturing method for manufacturing a device for electrochemically determining the presence of a polynucleotide. First and second substrates each comprise first and second surfaces are mated, wherein, when mated, the respective first surfaces define an electrochemical detection region therebetween. An electrode comprising an electrode surface is positioned so that the electrode surface is in liquid communication with the electrochemical detection region when the substrates are mated. At least one electrochemically active probe molecule is reversibly bound to the electrode surface, wherein the at least one electrochemically active probe molecule is a molecule that preferentially associates with double stranded polynucleotides as compared to single stranded polynucleotides. Wherein a first electrochemical signal indicative of an amount of electrochemically active probe molecule bound to the electrode surface may be obtained by applying an electrical potential to the electrode surface. If the electrode surface is contacted with a liquid comprising a double stranded polynucleotide, at least some of the probe molecules dissociates from the electrode surface and associates with the double stranded polynucleotide, wherein a second electrochemical signal indicative of an amount of electrochemically active probe molecule bound to the electrode surface may be obtained by applying an electrical potential to the electrode surface, a difference between the first and second electrochemical signals indicative of the presence of the double stranded polynucleotide. The electrochemical detection region may be dried (if wetted).

Another aspect of the invention relates to a microfluidic device for electrochemical detection of a polynucleotide. The device comprises a microfluidic network comprising a sample introduction passage for introducing sample material to the device, an electrochemical detection region, the sample introduction passage and the electrochemical detection region being connected by a second passage, the electrochemical detection region comprising an electrode surface, the electrode surface comprising a probe molecule reversibly immobilized with respect to the electrode surface, wherein the reversibly immobilized probe molecule is configured to, upon the electrode surface being contacted with a liquid comprising a polynucleotide comprising at least one duplex region, dissociate from the surface and associate with the polynucleotide, and wherein an electrochemical activity of probe molecule immobilized with respect to the electrode surface differs from an electrochemical activity of probe molecule associated with the polynucleotide. An electrical lead is in electrical communication with the electrode surface for accessing electrical signals from the electrode surface, wherein at least some of the electrical signals accessible from the electrode surface are indicative of an amount of probe molecule reversibly immobilized with respect to the electrode surface. A liquid motion device for moves sample material along the second passage between the sample introduction passage and electrochemical detection region. The electrochemical detection region may be dry prior to use.

An electrochemical detection system includes the microfluidic device and a connection port configured to receive the microfluidic device and provide electrical communication between at least (a) a processor and (b) first and second electrical leads of the device. The process is configured to receive a first electrical signal from the electrode surface, the first electrical signal indicative of an amount of probe molecule reversibly immobilized with respect to the surface, receive, upon the electrode surface being contacted with a liquid comprising a polynucleotide having at least one duplex region, a second electrical signal from the electrode surface, the second electrical signal being indicative of an amount of probe molecule reversibly immobilized with respect to the surface, and determine, based upon the first and second electrical signals, data indicative of the amount of the polynucleotide present in the electrochemical detection chamber.

Another aspect of the invention relates to a microfluidic device for electrochemical detection of first and second different target polynucleotides. The device comprises a microfluidic network, comprising a sample introduction passage for introducing sample material to the device, an electrochemical detection chamber, the sample introduction passage and the electrochemical detection chamber being connected by a second passage, the electrochemical detection chamber comprising an electrode surface, the electrode surface comprising first and second probe molecules reversibly immobilized with respect to the electrode surface, wherein each of the first and second probe molecules comprises (a) a respective electrochemically active portion having a respective, different oxidation-reduction potential and (b) a respective, different polynucleotide, the polynucleotide of the first probe molecule being complementary to at least a portion of the first target polynucleotide and the polynucleotide of the second probe molecule being complementary to at least a portion of the second target polynucleotide. Wherein the reversibly immobilized first and second probe molecules are each configured to, upon the electrode surface being contacted with a liquid comprising the first and second target polynucleotides, dissociate from the electrode surface, whereupon the polynucleotide of the first probe molecule forms a duplex region with the first target polynucleotide and the polynucleotide of the second polynucleotide forms a duplex region with the second target polynucleotide.

An electrical lead in electrical communication with the electrode surface provides access to electrical signals from the electrode surface, wherein a first subset of the electrical signals accessible from the electrode surface are indicative of an amount of the first probe molecule reversibly immobilized with respect to the electrode surface and a second subset of the electrical signals accessible from the electrode surface are indicative of an amount of the second probe molecule reversibly immobilized with respect to the electrode surface. A liquid motion device moves sample material along the second passage between the sample introduction passage and electrochemical detection chamber.

Another aspect of the invention relates to a method for detecting a target compound, which may be, e.g., a target polynucleotide. A first electrochemical signal is obtained from a first amount of probe molecule. A second electrochemical signal is obtained from a second amount of probe molecule.

In some embodiments, the method includes intermediate obtaining the first and second electrochemical signals, modifying an amount of target compound, e.g., target polynucleotide, in fluid communication with the first amount of probe molecule.

In some embodiments, the target compound is a target polynucleotide and the probe molecule has a first electrochemical activity when not intercalated with the target polynucleotide and a second, different electrochemical activity when intercalated with the target polynucleotide and wherein, upon modifying the amount of target polynucleotide, a portion $\Delta$ of the first amount of probe molecule intercalates with the target polynucleotide.

In some embodiments, the first and second amounts of probe molecule are not intercalated with the target polynucleotide when the electrochemical signals are obtained.

In some embodiments, the first and second amounts of probe molecule are reversibly immobilized with respect to an electrode and modifying the amount of target polynucleotide includes modifying the amount of target compound in communication with the first amount of probe molecule.

In some embodiments, the method includes using an electrode to obtain the first electrochemical signal and the same electrode to obtain the second electrochemical signal, the first and second electrochemical signals arising from a polynucleotide-free electrochemically active moiety of the probe molecule.

The first electrochemical signal may be obtained from a first amount of probe molecule in the presence of a first polynucleotide and a second polynucleotide, the first and second polynucleotides being sufficiently complementary to form a duplex. The method may include subjecting the first and second polynucleotides to at least one of an annealing step or a melting step in the presence of the first amount of probe molecule prior to obtaining the second electrochemical signal.

Upon modifying the amount of target compound, a portion $\Delta$ of the first amount of probe molecule associates with the target compound, the second electrochemical signal being different from the first electrochemical signal by an amount indicative of $\Delta$.

In some embodiments, the first and second electrochemical signals are obtained using an electrode and the second electrochemical signal is obtained without contacting the electrode with fresh probe molecule intermediate obtaining the first and second electrochemical signals.

One aspect of the invention relates to a dry electrode comprising an intercalating compound.

In some embodiments, an electrode includes a reversibly immobilized electrochemically active intercalating compound. The electrode may be essentially free of liquid. The electrode may be dry.

Another aspect of the invention relates to enclosure enclosing a dry electrode comprising an intercalating compound. The enclosure may be a flexible package.

BRIEF DESCRIPTION OF THE DRAWINGS

FIG. 3a is a side view of an electrochemical detection module illustrating probe molecules associated with a working electrode;

FIG. 3b is a side view of the electrochemical detection module of FIG. 3a illustrating the response of the probe molecules to a target compound;

FIG. 4 is a side view of an electrochemical detection module including an electrode having a layer defining an outer surface;

FIGS. 5a and 5b illustrate electrochemical detection of hybridization using a probe molecule and electrode;

FIG. 6b is a plot of the negative derivative with respect to temperature of a plurality of fluorescence signals obtained using an intercalating fluorophore present in the solution used to obtain the data of FIG. 6a;

FIG. 13 illustrates sequential electrochemical signals obtained from a reference sample with no target compound and from a sample including a target compound with conditioning of probe molecules after each signal acquisition.

DETAILED DESCRIPTION

Figure 1:
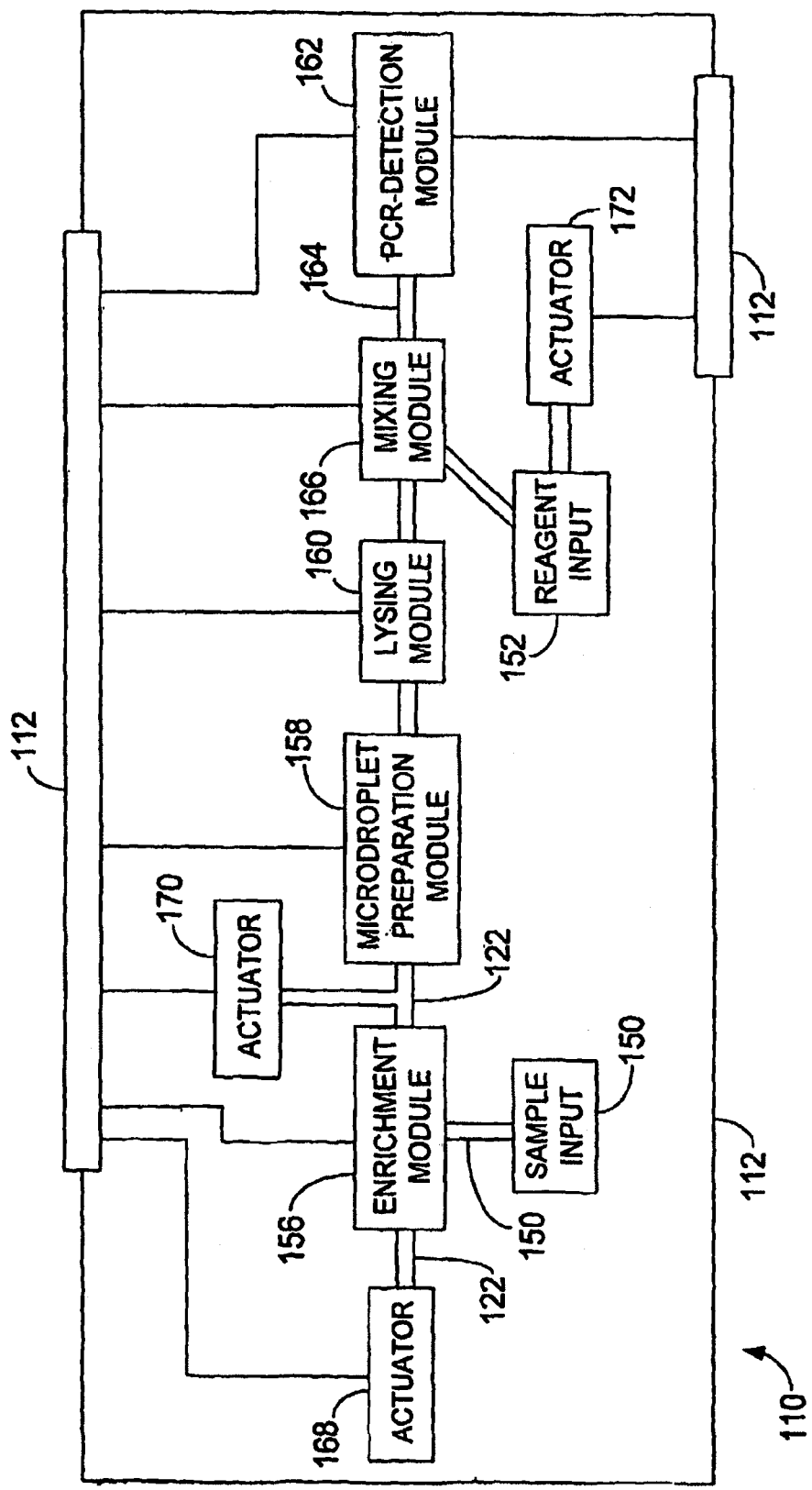
FIG. 1 shows a microfluidic network.

Referring to FIG. 1, a microfluidic network 110 of a microfluidic device includes modules to process a biological sample, such as to prepare the biological sample for detection of one or more target compounds thereof and to detect the target compound(s). Exemplary target compounds include DNA, RNA, and other polynucleotides. Proteins, viruses, and other biological compounds, such as those for which antibodies can be prepared may also be detected.

Microfluidic network 110 has a sample input module 150 and reagent input module 152 to allow sample and reagent materials, respectively, to be input to the network. Input modules 150, 152 are configured to allow automatic material input using a computer controlled laboratory robot. Microfluidic network 110 may also include output ports configured to allow withdrawal or output of processed sample material from or by the network.

Microfluidic network 110 includes process modules 156, 158, 160, 166 and 162 for subjecting biological samples to various physical and chemical processes and detection. For example, enrichment module 156 receives a biological sample having cells, bacteria, spores, fungi or other biological particles and prepares an enriched sample having a greater concentration of the biological particles. Lysing module 160 receives the enriched sample and releases intra-particle material, e.g., polynucleotides and/or proteins, from the biological particles. Mixing module 166 mixes sample materials, e.g., the released intra-particle material, with reagent materials. Detection module 162 detects one or more target compounds present in the intra-particle material. Where the target compound may be amplified, as may polynucleotides, detection module 162 may also be configured to amplify the target compound, such as by polymerase chain reaction (PCR), e.g., isothermal PCR or rolling circle PCR. Alternatively, the network may include a separate amplification module configured to amplify the target compound. Amplified material, e.g., amplicons, are output by the amplification module and received by the detection module.

Various modules of microfluidic network 110 are connected, such as by channels 164, to allow materials to be moved from one location to another within the network 110. Actuators 168, 170, 172 provide a motive force, such as a gas pressure and/or a vacuum, to move the sample and reagent material along the channels and between modules. For example, a first actuator 168 moves material downstream from process module 156 to process module 158. Upon completion of processing within process module 158, a second actuator 170 moves material downstream to mixing process module 160. Subsequently, actuator 170 or an additional actuator moves the material to mixing module 166, where the material mixes with reagent material moved by actuator 172.

Finally, actuator 172, or another actuator, moves the mixed material to module 162. Actuators generating a vacuum to move material need not create a region absent all gas or other material. Rather, the vacuum may be a region of reduced gas pressure as compared to another region of the microfluidic device.

The microfluidic network 110 may be defined using at least first and second substrates. Each substrate comprises a respective first surface. When mated, the respective first surfaces define the microfluidic network therebetween. At least one and optionally both of the first and second substrates may comprise a polymer, such as polyester. At least one of the substrates may comprise a polymer film such as a flexible lamina having a thickness of less than 1 mm, less than 0.75 mm, less than 0.5 mm, or even less than 0.25 mm. When one of the substrates is a lamina, the first surface of the other substrate generally comprises features that cooperate with the first surface of the lamina to define the microfluidic network therebetween. For example, the first surface of the other substrate may comprise any or all of grooves, channels, chambers and the like that are enclosed by the first surface of the lamina when the two substrates are mated.

A microfluidic network of a device may have any individual module or any combination of the modules and components of network 110. Exemplary microfluidic devices including such modules and components are disclosed in United States published patent application nos. 20030019522, filed Sep. 18, 2001 by Parunak, 20020142482, filed Dec. 14, 2001, by Wu et al., 20020141903, filed Dec. 14, 2001 by Parunak et al., and 20020142471, filed Feb. 15, 2002 by Handique et al., all of which applications are incorporated herein by reference in their entireties. A detection module including an electrode for electrochemical detection of target compounds is discussed next.

Detection Module Including an Electrode

Figure 2A:
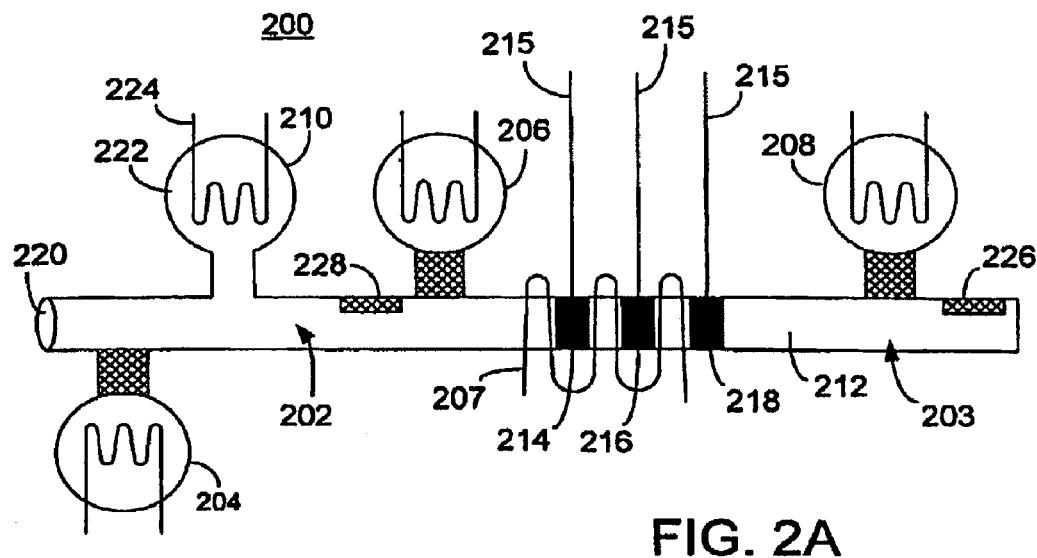
FIG. 2a shows an electrochemical detection module having integrated detection and amplification regions.

Referring to FIG. 2a, a detection module 200 detects the presence of one or more target compounds. Detection module 200 includes an upstream channel 202, an actuator 210, first, second, and third valves 204, 206, 208, and a downstream channel 203. Valves 206 and 208 define a detection region 212 therebetween. Typical detection regions have a volume of 100 µl or less, 50 µl or less, 10 µl or less, or 1 µl or less. Detection region 212 includes a working electrode 214, a reference electrode 216, and a counter electrode 218. The working electrode may be used alone or in any combination with the reference and counter electrodes to obtain electrochemical signals, e.g., signals indicative of the presence and/or identity of a target compound.

The reference electrode may be a standard reference electrode, such as a Ag/Ag—Cl electrode. The counter electrode may be made of any conductive material, such as platinum or palladium. Electrodes 214, 216, and 218 include leads 215 that provide electrical communication with the electrodes.

In certain embodiments, working electrode 214 is associated with a plurality of probe molecules having an electrochemical activity that depends upon the presence or absence of a target compound. For example, the target compound may modify the electrochemical activity of the probe molecule by modifying the number of probe molecules in electrochemical communication with the electrode. Alternatively or in combination, the target compound may modify an electrochemical characteristic of the probe molecule itself For example, interaction between the probe molecule and the target compound may modify an oxidation or reduction potential of an electrochemically active moiety of the probe molecule. To determine the presence of the target compound, the working electrode is used to obtain one or more electrochemical signals from the probe molecules. The electrochemical signal(s) are used to determine the presence or absence of the target compound.

In use, sample material comprising a target compound is input to detection module 200 via an input 220. Valve 204 is configured in a normally open state that allows passage of material, e.g., sample material, between input 220 and upstream channel 202. Material input to detection module 200 travels generally along upstream channel 202 toward detection region 212. Once material has been received along channel 202, valve 204 may be actuated to a closed state, which obstructs the passage of material between input 220 and upstream channel 202.

Actuator 210 moves material further downstream within microfluidic network 110. Actuator 210 includes a gas chamber 222 and a heat source 224 configured to heat material within chamber 222 to generate gas having an increased pressure. With valve 204 in a closed state and valves 206 and 208 in the open state, the increased gas pressure moves material generally downstream toward detection region 212. Downstream channel 203 may include a vent 226, which limits or prevents pressure build up downstream of the sample material from inhibiting movement of the sample. Vent 226 may be a porous hydrophobic material that allows gas to exit channel 203 but inhibits the passage of aqueous liquids and sample components.

Upstream channel 202 includes a second vent 228. When an upstream terminus of the sample material moved downstream by actuator 210 passes vent 228, the gas providing the motive force to the sample material exits vent 228 thereby removing the motive force. Thus, at least a portion of the sample material is positioned generally within detection region 212. Vent 228 may be a porous hydrophobic material as vent 226.

Prior to the introduction of sample material to detection region 212, electrode 214 may be dry, e.g., liquid may be absent or essentially absent from detection region 212. Liquid, if present, generally does not contact electrode 314 and may have a volume of less than about 10%, less than about 5%, less than about 2%, or less than about 1% of detection region 212. Sample material introduced to detection region 212 communicates with electrode 214 and/or probe molecules associated therewith so that the electrodes can be used to obtain one or more electrochemical signals with which the presence of the target compound(s) may be determined. Sample material may also communicate with other electrodes if present.

Detection module 200 may be configured to amplify target polynucleotides of the biological sample. In such embodiments, detection module 200 is associated with a heat source 207 in thermal contact with the detection region 212. Heat source 207 is configured to heat material within detection region 212 by an amount sufficient to melt double stranded target polynucleotides to be amplified. Upon introducing the sample material to detection region 212, valves 206, 208 may be actuated to the closed state to limit or prevent sample material and gas from exiting the detection region during heating. U.S. Pat. No. 6,132,580 to Mathies et al., which patent is incorporated herein by reference, discloses devices for amplifying polynucleotides.

Figure 2B:
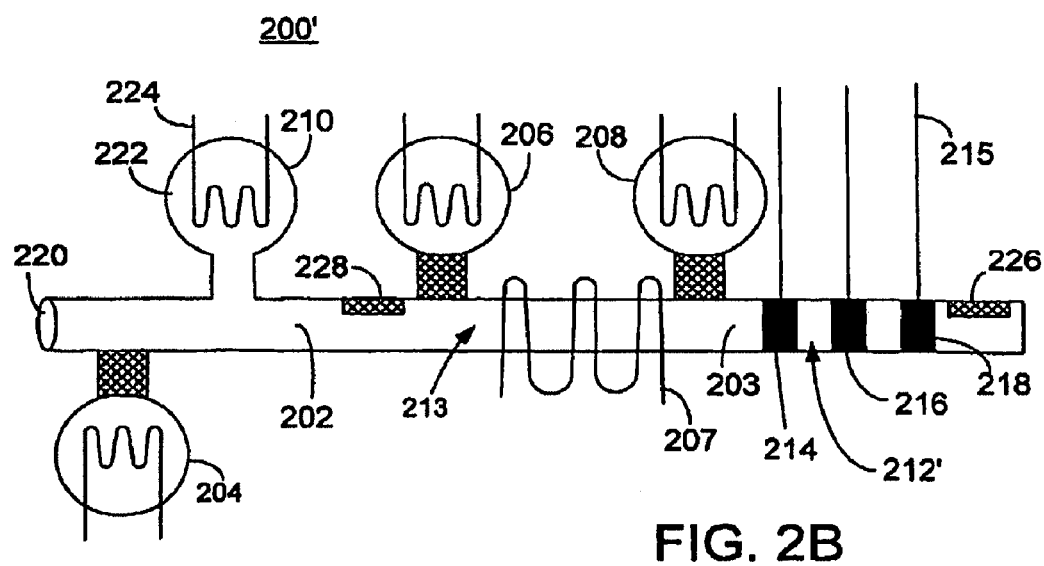
FIG. 2b shows an electrochemical detection module having spaced-apart detection and amplification regions.

Referring to FIG. 2b, a detection module 212' includes a detection region spaced apart from an amplification region 213 configured to amplify polynucleotides of a sample. Sample material is received by amplification region 213 via input 220 and upstream channel 202. Valves 206 and 208 seal amplification region 213 during amplification. Intermittently during amplification, or upon the completion thereof, valve 208 is opened and an aliquot of amplified material is introduced to detection region 212'. Electrode 214 is used to detect the amplified polynucleotide. Actuator 210 may provide the motive force to move the amplified material. Valve 208 is resealable so that amplification can be renewed without evaporative loss of material.

Working Electrode and Probe Molecules

Referring to FIG. 3a, electrode 214 includes a probe molecule 232 associated with a surface 230 of the electrode. Referring also to FIG. 3b, probe molecule 232 may be reversibly immobilized with respect to electrode 214 such that, in the presence of a target compound, e.g., a single or double stranded polynucleotide 233, probe molecule 232 dissociates from electrode 214 and interacts with the target compound. In the presence of a target compound, the probe molecule preferentially associates with the target compound as opposed to the electrode. In the absence of a target polynucleotide, the probe molecule tends to re-associate with the electrode. Thus, in the presence of a target compound, the amount of probe molecule 232 immobilized with respect to the electrode 214 decreases (FIG. 3b) whereas in the presence of smaller amounts of the target compound, or its absence, (FIG. 3a), the amount of probe molecule immobilized with respect to the electrode remains constant or decreases at a smaller rate.

Probe molecule 232 can be detected electrochemically using electrode 214. An electrochemical activity of the probe molecule and/or an amount of probe molecule in electrochemical communication with the electrode 214 depends upon the presence or absence of the target compound. Thus, the target compound may be detected using one or more electrochemical signals from the probe molecule. In certain embodiments, first and second electrochemical signals are obtained. At least one of the electrochemical signals is obtained in the presence of an amount of the target compound (the amount will be zero if the target compound is absent). In some embodiments, a known amount of target compound is present when the first electrochemical is obtained. Generally, the amount of target compound is modified intermediate obtaining the first and second electrochemical signals. Detection of the target compound is determined based upon a difference between the first and second electrochemical signals.

In some embodiments, a first electrochemical signal is obtained in the presence of an amount of the target compound. Detection of the target compound is determined by comparing the first electrochemical signal to a reference signal. The reference may be a reference electrochemical signal obtained from a reference sample and may be obtained using a different electrode, e.g., a second working electrode located in a second sample detection region of a second detection module having a structure similar to detection module 200.

Electrochemical signals may be obtained from probe molecule 232 by, e.g., applying a potential to electrode 214 to reduce or oxidize probe 232. A current results from the reduction or oxidation of the probe molecule. A typical electrochemical signal is a square wave voltammogram (SWV) although other forms of electrochemical signals may be obtained. Probe molecule that is oxidized (or reduced) in obtaining the electrochemical signal may generally be reduced (or oxidized) by reversing the potential applied to the electrode.

In certain embodiments, the probe molecule is an intercalator, which intercalates with target compounds having a duplex region such as double stranded DNA. Alternatively, the probe molecule may be a groove binder, such as a minor groove binder or triplex groove binder. The intercalator or groove binder preferentially associates with double stranded polynucleotides as opposed to re-associating with the electrode.

In some embodiments, the probe molecule includes a polynucleotide portion having a sequence complementary to a sequence of a target polynucleotide. In the presence of the target polynucleotide, the sequence of the probe molecule and the sequence of the target polynucleotide form a duplex, which formation tends to inhibit the probe molecule from re-associating with the electrode and/or reduces the electrochemical activity of the probe molecule.

In some embodiments, the probe molecule includes an antibody or antigen that exhibits specific association, e.g., binding, with a particular target compound or group of target compounds. In the presence of the target compound, the antibody or antigen of the probe molecule associates with the target compound, which association tends to inhibit the probe molecule from re-associating with the electrode and/or reduces the electrochemical activity of the probe molecule.

In some embodiments, the probe molecule has an electrochemically active moiety that is free of polynucleotides and may be free of purines. An electrochemical signal free of contribution from the oxidation or reduction of purine-containing groups may be obtained from the probe molecule. Even where the probe molecule includes one or more purine groups, an electrochemical signal essentially free or free of contribution from the oxidation or reduction of the purine groups may be obtained by applying a potential difference that avoids oxidizing or reducing purine groups. An electrochemical signal that is essentially free of contribution from purine groups comprises at least about 75%, e.g., at least about 95% of signal from the probe molecule. For example, an electrochemical signal essentially free or free of contribution from oxidation or reduction of purine groups may be obtained by applying at least one potential difference between about −1.2 V and about 1 V as against a Ag/AgCl reference electrode may be applied to avoid or limit oxidation of guanine groups. Even where the electrochemical signal obtained from the electrode comprises a greater contribution from purine groups, a modified signal essentially free of the contribution from the purine groups may be extracted by mathematical processing. The target compound may be detected based upon the modified signal.

In some embodiments, the electrochemical signals obtained from the probe molecule do not arise from an electrochemical process that is amplified enzymatically. This embodiment does not of course exclude the electrochemical detection of polynucleotides amplified by, for example, PCR reaction.

Probe molecules typically include a group that associates, e.g., by adsorption, with carbon. Typical groups include substantially planar or flat aromatic compounds comprising at least one of a benzyl group, a napthyl group, an anthracyl group, a chrysene group, a benxo[a]anthracene group, a phenanthryl group, or derivatives thereof. Dihydroxy, dicarbonyl, or amino derivatized groups are typical.

Exemplary probe molecules include nogalamycin, 6,7-dichloro-1,4-dihydroxyanthraquinone, carminic acid, hydroquinidine (anthraquinone-1,4-diyl)diether, hydroquinine (anthraquinone-1,4-diyl)diether, 2,3-dimethylquinizarin, 5,8-dichloro-1,4-dihydroxyanthraquinone, 1,2,3,4-tetrafluoro-5,8-dihydroxy-anthraquinone, 6,11-dihydroxy-5,12-naphthacenedione, 3-bis-bromomethyl-1,4-dihydroxy-anthraquinone, 8-acetyl-6,11-dihydroxy-7,8,9,10-tetrahydro-naphthacene-5,12-dione, 4-dimethoxy-anthraquinone, acetic acid 4-acetoxy-9,10-dioxo-9,10-dihydro-anthracen-1-yl ester, 1,4-dihydroxy-5,8-bis-(2-hydroxy-ethylamino)-anthraquinone, quinalizarin, 4-dihydroxy-5,8-di-p-toluidinoanthraquinone, anthraquinone, 1,2,4-trihydroxy, (dhq)2aqn, (dhqd)2aqn, quinizarin, daunomycin, doxorubicin, methylene blue, toluidine blue O, azure A, azure B, azure C, ethidium, daunomycin, actinomycin D, distamycin, netropsin, DAPI, BePI, coralyne, berberine, TMPyP, TriM-TMPyP, anthracyclines, NMM, berenil, chromomycin, 1-pyrenemethylamine, thionin, and derivatives thereof. Derivatives of such probe molecules include derivatives including a polynucleotide strand having a sequence complementary to a sequence of a target polynucleotide.

A probe molecule, e.g. an anthracycline, may be associated with a working electrode by adsorption from a solution. For example, the electrode may be contacted with a solution comprising a sufficient amount of the probe molecule to adsorb an electrochemically detectable amount of the probe molecule on to the electrode, with the electrochemically detectable amount remaining even after the solution comprising the probe molecule is removed from contact with the electrode. Typically solutions have a concentration of at least about 0.5 µM, at least about 5 µM, e.g., about 20 µM probe molecule. The solutions may have a probe molecule concentration of about 250 µM or less, e.g., about 100 µM or less. In some embodiments, the solution is a buffer solution, e.g., a 5 mM sodium phosphate buffer at pH 7. The solution may be prepared by using the buffer to dilute an acidic solution, e.g., a 5% acetic acid solution, comprising about 1 mM probe molecule. The electrode is contacted with the about 20 µM probe molecule solution, e.g., with about 0.25 µl per mm$^2$ of electrode. The solution is allowed to dry. Typically, about 50 femtomoles of probe molecule are associated per mm$^2$ of electrode. The electrode may be rinsed with agitation with distilled water and again allowed to dry. The electrode is generally stored at ambient temperatures and in the dark until ready for use. The electrode may be contacted with water and/or a buffer solution prior to contacting with a solution comprising a target compound to be detected.

In some embodiments, the electrode comprises a surfactant, e.g., a cationic surfactant such as hexadecyltrimethylammonium bromide (CTAB). An electrode comprising a probe molecule and a cationic surfactant may be prepared by adsorbing these species to an electrode from a single solution or sequentially from several solutions. In one embodiment, a saturated solution of cationic surfactant, e.g., CTAB, is prepared. The saturated solution is diluted, e.g., 1:1, with a solution of probe molecule, e.g., DOX in 5 mM sodium phosphate buffer pH 7.0. The electrode is contacted with the diluted solution and allowed to dry, generally at room temperature but the electrode may be baked at a temperature typically less than the boiling point of the solution. The dried electrode may be agitated in water. The electrode may be dried mechanically, e.g., with a adsorbent medium such as a tissue.

An electrode associated with a probe molecule may be used to detect the presence of amplicons formed by amplifying a target polynucleotide. Typically, a sample of target polynucleotide to be amplified includes N copies of the polynucleotide. During each amplification cycle, the target polynucleotide is amplified with an efficiency ε resulting in NHε$^C$ amplicons after C cycles. Typical target polynucleotides to be amplified are present in an amount of about N=1000 copies.

Using an electrode associated with a probe molecule, e.g., an anthracycline, a concentration differential of about 200 pico molar polynucleotide is sufficient to cause a difference between first and second electrochemical signals. Given a sample comprising N=1000 copies of polynucleotide, about 22 amplification cycles with an efficiency of $\epsilon$=1.7 in a volume of about 10 micro liters is sufficient to generate a target polynucleotide concentration of 200 pico molar. In other embodiments, a concentration differential of as low as 5 nanomolar, as low as 1 nanomolar, e.g. as low as 500 pico molar is sufficient to cause a difference between first and second electrochemical signals allowing the polynucleotide to be detected.

In some embodiments, the probe molecule is subjected to a conditioning step to increase the sensitivity of the probe molecule with respect to the target compound. In general, conditioning is performed prior to obtaining an electrochemical signal. Typically, the conditioning step includes applying a conditioning potential to the probe molecule that is greater in magnitude than a potential used to obtain electrochemical signals from the probe molecule. The conditioning potential may be sufficient to modify a reduction or oxidation state of the probe molecule and may generate a radical therefrom. In some embodiments, the probe molecule is an anthracycline, e.g., doxorubicin (DOX).

In one embodiment, an electrode including reversibly immobilized DOX is contacted with a buffer, e.g., 5 mM phosphate buffer. A first electrochemical signal is obtained, as by SWV, e.g., a ramp between −0.2 and −1.2 V using a 3 second scan (against Ag/AgCl). An amount of target compound is introduced to a detection region including the electrode. The target compound may be introduced as a mixture suitable for amplifying the target compound. A second electrochemical signal is obtained, as by SWV. A conditioning potential is applied to the electrode as by chronoamperometry, e.g., a potential of about −1.3 V for about 5 seconds is applied to the electrode. If an amplifying mixture was introduced, the mixture may be subjected to one or more amplification cycles in the presence of the electrode. After a number of cycles, an electrochemical signal is obtained, as by SWV and the electrode is again subjected to a conditioning potential. The steps of amplification, obtaining an electrochemical signal, and conditioning may be repeated, e.g., 5 times, 10 times, 20 times or more. The presence or absence of the target compound may be determined using any combination of the electrochemical signals.

The working electrode 214 is typically a carbon electrode. For example, one or more of the electrodes may include glassy carbon, graphite, carbon fiber, carbon paste, or vitreous carbon, such as reticulated vitreous carbon. A carbon material may be combined with a filler, e.g., a polymer to prepare the electrode. The carbon material may be combined with the probe molecule as a flowable mixture to prepare the electrode. In some embodiments, carbon are prepared by screen printing a conductive ink. The ink may be printed on a substrate, e.g., a polyester substrate, and a polyester lamina mated with the substrate to seal the printed electrode. The conductive ink may include the probe molecule. In addition to or as an alternative to carbon, the working electrode may include other materials, e.g., a metal capable of reversibly binding with the probe molecule, e.g., gold or platinum.

In certain embodiments, a working electrode is provided with a probe molecule during manufacture and prior to delivery to a user. The electrode may be dry during shipping. The electrode may be enclosed within an enclosure, e.g., a foil or polymer that may be flexible.

The reference electrode may be any reference electrode, such as a Ag/AgCl electrode. The counter electrode may be formed of any suitable conductive material, such as Pd. Other suitable materials for any of the electrodes include carbon, gold, silver, and platinum. At least one of the electrode surface, probe molecule, and liquid comprising the target compound may be free of organic transition metal complexes comprising pyridine groups or free of all organic transition metal complexes.

In one embodiment, the working electrode surface is substantially free of crystalline material. For example, the working electrode surface may be substantially amorphous. In another embodiment, the working electrode surface may be substantially free of amorphous material.

Referring to FIG. 4, a detection region 212' includes an electrode 240 having a substrate 242 and a layer 244, and electrodes 216, and 218. Detection region 212' may be located within a detection module otherwise similar to detection module 200. Substrate 242 is generally a conductive material including, for example, at least one of a metal, a polymer, carbon, or the like. Lead 215 facilitates acquisition of electrochemical signals from electrode 240.

Layer 244 may include a conductive material that provides electrochemical communication between probe molecule 232 associated with a surface 246 of electrode 240 and a surface 248 of substrate 242. For example, the conductive material may allow a current to flow between probe molecule 232 and substrate 242. Exemplary conductive materials include conductive polymers, polyalcohols (for example a polyvinyl alcohol), polyacids (for example a polyacrylic acid), or combinations thereof. Derivatives of such materials are also suitable. The conductive material may be ionizable.

The conductive material may be impermeable or permeable with respect to a liquid comprising the target compound. Preferably, however, the conductive material is permeable and the liquid contacts the surface 248 of substrate 242.

If layer 244 and substrate 242 are formed of different materials, layer 244 may act as a catalyst that modifies a potential at which the probe molecule is oxidized or reduced as compared to a potential at which the probe molecule 232 would be oxidized or reduced at surface 248 of substrate 242. For example, layer 244 may reduce an absolute magnitude of an oxidation or reduction potential of the probe molecule.

Layer 244 may include a non-conductive material, which nonetheless provides electrochemical communication between surface 246 and substrate 242. For example, a non-conductive layer 244 may be permeable with respect to at least one of the probe molecule and the liquid used to introduce the target compound.

Electrochemical Detection of Hybridization

Referring to FIGS. 5a and 5b, hybridization of a polynucleotide may be determined electrochemically using an electrochemical detection module defining an electrochemical detection region, e.g., region 212, having an electrode 214 as discussed above. A first target polynucleotide 275 and a complementary polynucleotide 277 are introduced to the electrochemical detection chamber. The polynucleotides may be introduced by actuating a gas actuator connected to the detection region. The polynucleotides may be introduced within the detection region by amplification.

The polynucleotides 275, 277 are sufficiently complementary to one another to form a duplex 279. For example, the polynucleotides may have complementary sequences of at least 8 bases, at least 16 bases, for example, at least 30 bases in length. The duplex has a melting temperature at which 50 percent of duplexes are denatured.

In some embodiments, probe molecule 232 is present within detection region 212 prior to introducing the polynucleotides. For example, the probe molecule 232 may be immobilized with respect to electrode 214, such as by being reversibly bound thereto (FIG. 5a). In other embodiments, the probe molecule is introduced to the electrochemical detection region with the one or both polynucleotides 275, 277 or independently thereof.

A first electrochemical signal indicative of the electrochemical activity of the first probe molecule is obtained with the polynucleotides 275, 277 at a first temperature. When the first probe molecule is (i) in the presence of the polynucleotides 275, 277 and (ii) at a temperature below a melting point of the duplex 279, the probe molecule 232 has a first electrochemical activity (FIG. 5b). When the probe molecule 232 is (i) in the presence of the polynucleotides 275, 277 and (ii) at a temperature above the melting point of the duplex 279, the probe molecule 232 has a second, different electrochemical activity with respect to the electrode. In some embodiments, the probe molecule is an intercalating compound or groove binder and associates with the double stranded DNA modifying an electrochemical activity of the probe molecule and/or an amount of probe molecule available to the electrode.

The fraction of polynucleotides 275, 277 cooperating to form duplex 279 may be modified by modifying physiochemical conditions present in the electrochemical detection chamber. For example, the amount of duplex 279 present in the electrochemical detection chamber may be decreased by increasing the temperature or changing the amount of chemical denaturant present within the electrochemical detection chamber. Decreasing the amount of duplex 279 decreases the amount of probe molecule 232 associated with the duplex. The melting point of a duplex may be determined by obtaining electrochemical signals as a function of, for example, temperature or amount of chemical denaturing agent present within the electrochemical detection chamber.

Figure 6A:
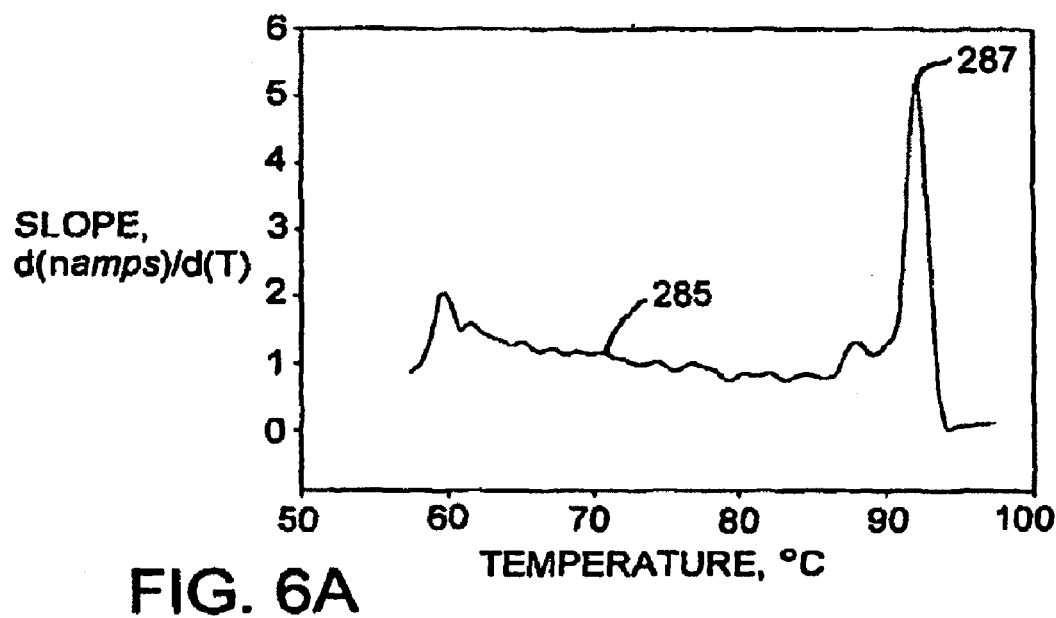
FIG. 6a is a plot of the derivative with respect to temperature of a plurality of electrochemical signals obtained from a probe molecule in communication with a solution including complementary polynucleotides.
Figure 6B:
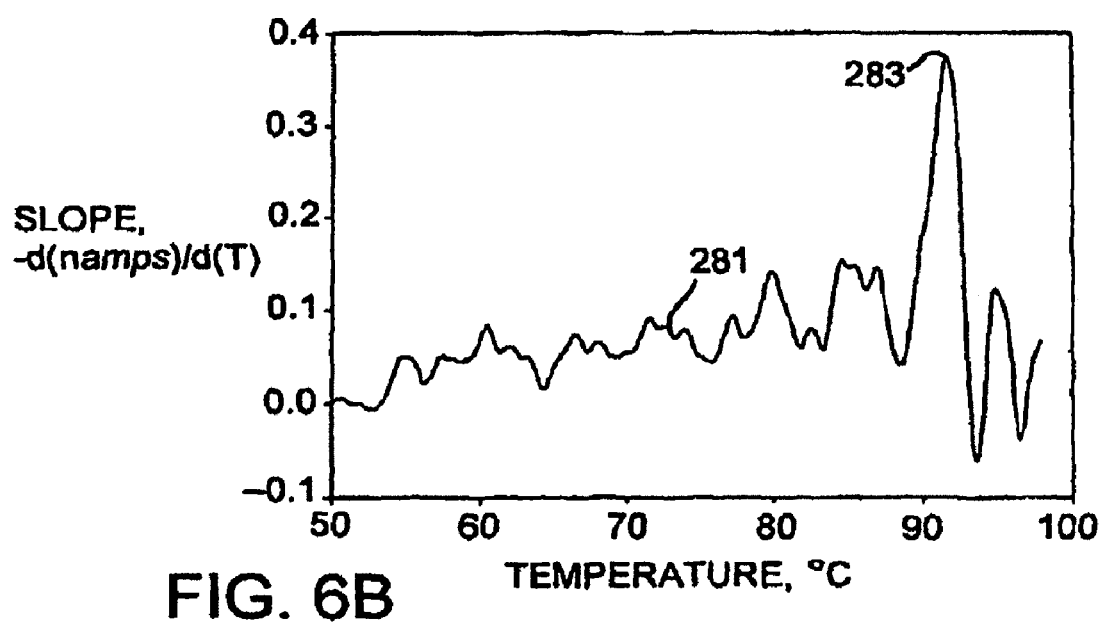

Referring to FIGS. 6a and 6b, the presence or absence of hybridization may be determined by obtaining electrochemical signals as a function of temperature. In FIG. 6b, a slope 281 of a plurality of electrochemical signals obtained from a solution including complementary polynucleotides exhibits a peak 283 at a temperature of about 92° C. indicating a change in the electrochemical signals. The change is indicative of the melting of the double stranded polynucleotide at temperatures about 92° C. Upon melting the double stranded polynucleotide, once intercalated probe molecule is detected with greater efficiency resulting in an increased electrochemical signal.

In FIG. 6a, a negative slope 285 of a plurality of fluorescence signals obtained from the same solution also exhibits a peak 287 a temperature of about 92° C. The fluorescence signals were obtained from an intercalating dye, which fluoresces when intercalated with the double stranded polynucleotide present at temperatures below 92° C. and does not fluoresce in the absence of the double stranded polynucleotide.

In some embodiments, the method includes introducing at least a second target polynucleotide and a second complementary polynucleotide to the electrochemical detection region. The second target polynucleotide and the second complementary polynucleotide are sufficiently complementary to one another to form a second duplex. A second probe molecule may also be introduced. Alternatively, the second probe molecule may already be associated, such as by reversible binding, with the electrode surface. Preferably, when the second probe molecule is (i) in the presence of the second target polynucleotide and the second complementary polynucleotide and (ii) at a temperature below a melting point of the second duplex, the second probe molecule comprises a second electrochemical activity with respect to the electrode surface and, when the second probe molecule is (i) in the presence of the second target polynucleotide and the second complementary polynucleotide and (ii) at a temperature above the melting point of the second duplex, the second probe molecule comprises a second, different electrochemical activity with respect to the electrode surface.

A third electrochemical signal is obtained. The third electrochemical signal is indicative of the electrochemical activity of the second probe molecule. The third electrochemical signal is obtained with the second target polynucleotide and the second complementary polynucleotide at a second temperature. After obtaining the third electrochemical signal, if the second temperature was less than the melting point of the second double stranded polynucleotide, increasing the temperature of the second duplex to a temperature greater than the melting point of the second duplex. On the other hand, if the second temperature was greater than the melting point of the second duplex, decreasing the temperature of the second target polynucleotide and the second complementary polynucleotide to a temperature less than the melting point of the second duplex.

Then, a fourth electrochemical signal indicative of an electrochemical activity of the second probe molecule is obtained. The presence of the second target polynucleotide is determined based on the third and fourth electrochemical signals.

Detecting Multiple Target Compounds

Referring to FIGS. 7a-7e, a plurality of target compounds are detected electrochemically using probe molecules 1160 and 1162, which respectively comprise a first portion 1164, 1166 and a second portion 1168, 1170. First portions 1164, 1166 may be identical to one another and may include any of the probe molecules discussed herein. Second portion 1168 of probe molecule 1160 preferentially associates with a first target molecule, e.g., polynucleotide 1161, as opposed to a second, different target molecule, e.g., polynucleotide 1163. Second portion 1170 of probe molecule 1162 preferentially associates with second polynucleotide 1163 as opposed to first polynucleotide 1161.

The first portions 1164, 1166 typically have an electrochemically activity that depends upon the presence or absence of the particular target compound to which the second portion preferentially associates. The probe molecules are typically used in combination with an electrochemical detection region 1154, which may be identical with electrochemical region 212 or 212' and includes an electrode 1150, which may be identical to electrode 214. Electrode 1152 may include an optional layer, e.g., a layer 244, which may or may not be conductive. Probe molecules 1160, 1162 are typically associated with electrode 214, such as being reversibly immobilized thereto. In the absence of a target compound particular to the second portion of the probe molecule, the probe molecule tends to remain immobilized with respect to the electrode. As the abundance of the particular target compounds increases, the amount of probe molecule associated with the electrode decreases and the amount associated with the target compound increases (FIGS. 7a-7e).

Although FIGS. 7a-7e show a single electrode 214 having probe molecules immobilized with respect thereto, electrochemical detection region 1154 may include one or more additional working electrodes each having one or more respective probe molecules reversibly immobilized. The respective probe molecules of different electrodes may selectively associate with different target compounds. In such embodiments, electrochemical signals indicative of the presence of the different target compounds are obtained from the different working electrodes. Thus, a plurality of target compounds can be simultaneously determined even where the electrochemical activities of the probe molecules cannot be distinguished. Region 1154 may also include with one or more reference electrodes 1151, which may be identical with either of electrodes 216 and 218.

The electrochemical activities of first portions 1164 and 1166 may be different so that the first portions can be distinguished electrochemically. Thus, either of probe molecules 1160, 1162 may be determined independently in the presence of the other of probe molecule. In certain embodiments, electrochemically active portions 1164, 1166 have different oxidation-reduction potentials. In this case, each of probe molecules 1160, 1162 may be distinguished from the other probe molecule by, for example, applying different potentials to electrode 1150. The different potentials may be applied by sweeping or scanning the potential. Preferred active portions have oxidation potentials of at least −1.2 volt, for example at least −0.7 volts. Preferred active portions have oxidation potentials of less than 1.0 volts, for example, less than 0.7 volts.

The association between the respective second portion of each probe molecule and the target compound is typically greater than an association between the probe molecule and the electrode. If target polynucleotide 1161 is not present in the liquid contacting electrode 214, substantially all of first probe molecule 1160 remains reversibly immobilized with respect to the electrode. If second target polynucleotide 1163 is not present in the liquid contacting the electrode, substantially all of second probe molecule 1162 may remain reversibly immobilized with respect to the electrode.

It should be understood that some of one or both probe molecules 1160, 1162 may be free of the electrode surface 214 even in the absence of the first and second compounds to be determined. For example, some of probe molecules 1160, 1162 may be free of are may become freed, such as by dissociation, from electrode 214 prior to introduction of the first and second target compounds. Upon the introduction of first and second target compounds, a detectable change occurs in a respective electrochemical signal resulting from probe molecules 1160, 1162. The change in the respective electrochemical signals generally results because the amount of probe molecule associated with the electrode decreases upon the introduction of the target compounds.

Second portions 1168, 1170 are configured to associate selectively with different target compounds. For example, where the target compound is a virus or bacteria, the second portion may comprise an antibody to the virus or bacteria. Where the target compounds are target polynucleotides 1161, 1163, as in FIGS. 7a-7e, the second portions preferably comprise respective polynucleotides 1168, 1170. The second portions may comprise oligonucleotides. Polynucleotide 168 of probe molecule 1160 is complementary to at least a portion of the first target polynucleotide 1161. Polynucleotide 1170 of probe molecule 1162 is complementary to at least a portion of the second target polynucleotide 163. Polynucleotides that are at least partially complementary to one another may associate by, for example, hybridizing to form one or more duplex regions, such as a double stranded DNA.

Probe molecules 1160, 1162 may be used to detect target compounds as follows. A first electrochemical signal is obtained. The first electrochemical signal may be a reference electrochemical signal indicative of the amount of the first probe molecule reversibly immobilized with respect to the electrode surface. Alternatively, or in addition, the first electrochemical signal may be a reference electrochemical signal indicative of a reference response of the electrode. For example, the reference electrochemical signal response may be indicative of the response that would be observed when a liquid comprising a known amount, for example, none, of a first target compound is introduced to region 1154.

A second electrochemical signal is obtained. The second electrochemical signal may be a reference electrochemical signal indicative of the amount of the second probe molecule reversibly immobilized with respect to the electrode surface. Alternatively, or in addition, the second electrochemical signal may be a reference electrochemical signal indicative of a reference response of electrode 214. For example, the reference electrochemical signal response may be indicative of the response that would be observed when a liquid comprising a known amount, for example, none, of the second target compound is introduced to region 154.

Electrode 214 is contacted with a preferably liquid sample comprising at least one of the first and second target polynucleotides 1161, 1163. If the first target polynucleotide 1161 is present in the sample, at least some of the first probe molecule 1160 immobilized with respect to the electrode dissociates therefrom. Polynucleotide 1168 of first probe molecule 1160 associates, such as by hybridization, with first target polynucleotide 1161 to form a duplex 1172. If second polynucleotide 1163 is present in the sample, at least some of second probe molecule 1162 immobilized with respect to the electrode dissociates therefrom. Polynucleotide 1170 of second probe molecule 1162 may associate, such as by hybridization to form a duplex 1174, with second target polynucleotide 163.

A third electrochemical signal is obtained, generally after at least one of (a) introducing to region 1154 the sample comprising at least one of the first and second target polynucleotides 1161, 1163. The sample typically contacts the electrode when introduced. The third electrochemical signal may be a sample electrochemical signal indicative of the amount of the first probe molecule 1160 reversibly immobilized with respect to the electrode. Alternatively, or in addition, the third electrochemical signal may be a sample electrochemical signal that may be compared with a reference response of the electrode to determine the amount of first target polynucleotide 1161 present in the liquid. A fourth electrochemical signal may be obtained from the second probe molecule 1162 in a similar fashion.

The presence of first target polynucleotide 1161 may be determined using the third and, optionally, the first electrochemical signal. For example, a change, such as a decrease, in a current associated with an oxidation or reduction potential of probe molecule 1160 is indicative of the presence of polynucleotide 1161. The presence of second target polynucleotide 1163 may be determined using the fourth and, optionally, the second electrochemical signal. For example, a change, such as a decrease, in a current associated with an oxidation or reduction potential of probe molecule 1162 is indicative of the presence of polynucleotide 1163.

Figure 7A:
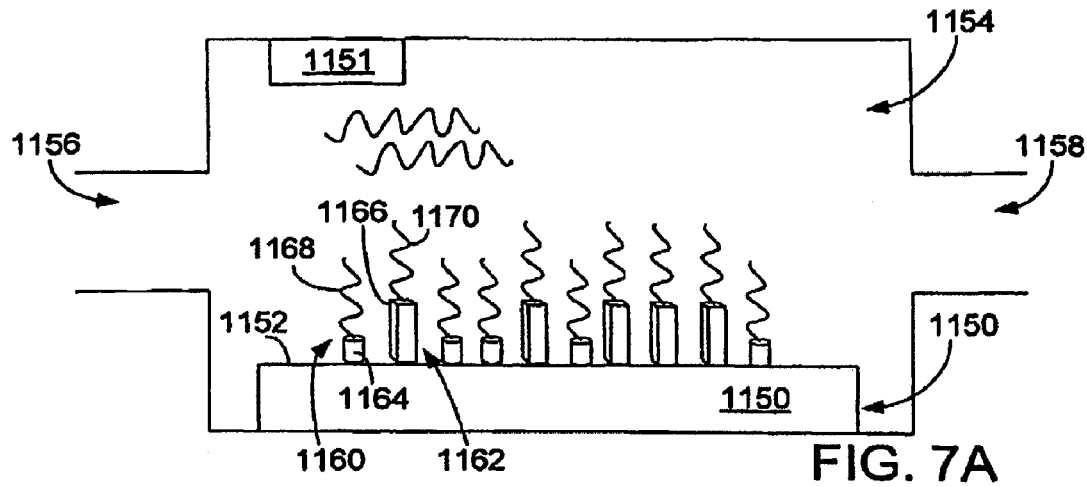
FIGS. 7a-7e illustrate electrochemical detection of two different target compounds using two different probe molecules.
Figure 7B:
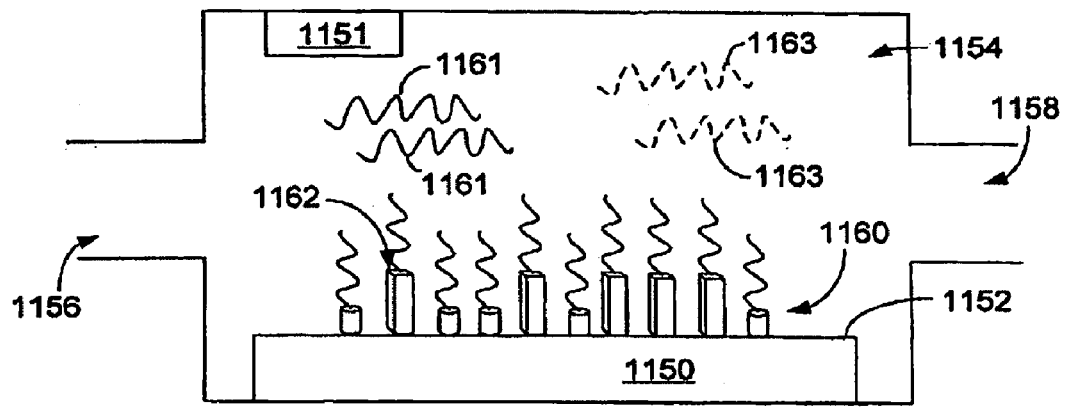
Figure 7C:
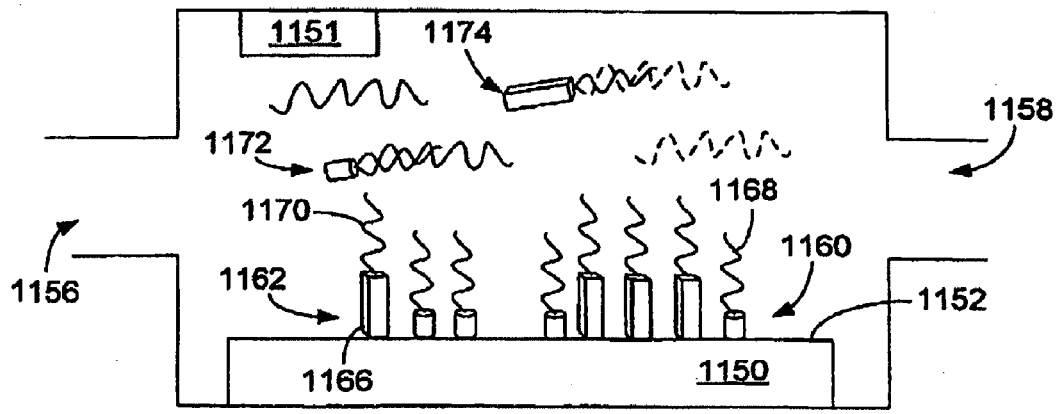
Figure 7D:
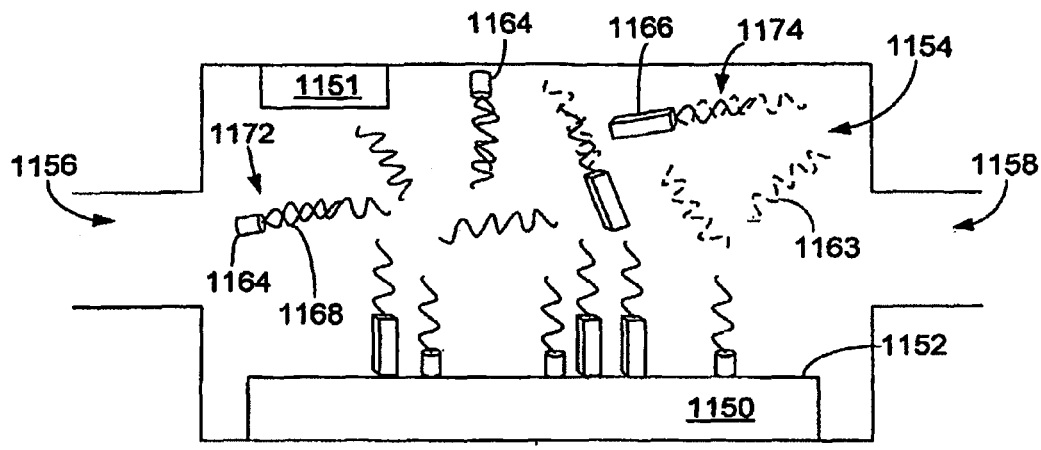
Figure 7E:
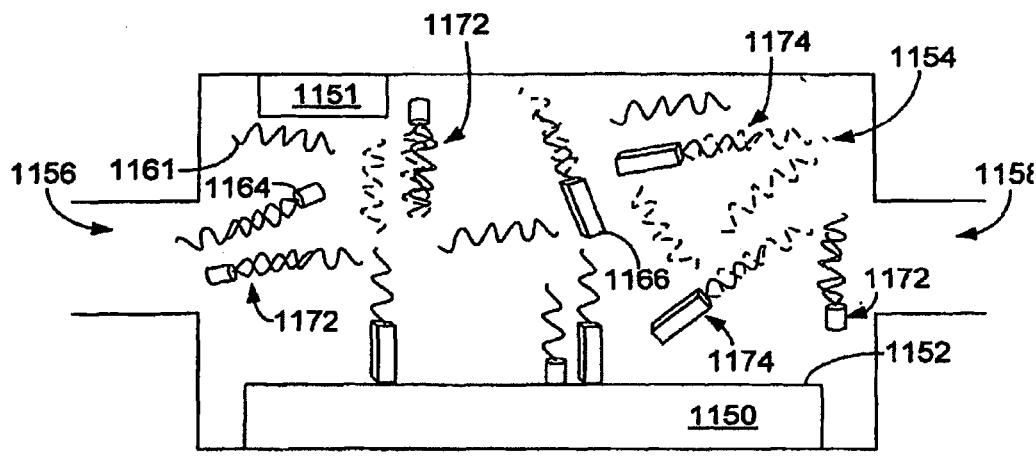

Referring to FIG. 7a, region 1154 is shown prior to introducing either of target polynucleotides 1161 or 1163 thereto. Substantially all of probe molecules 1160 and 1162 are reversibly immobilized with respect to electrode 214. Referring to FIG. 7b, a first amount of target polynucleotides 1161, 1163 has been introduced to region 1154. Referring to FIG. 7c, at least some of probe molecules 1160, 1162 have dissociated from the electrode and associated, by hybridization, with respective target polynucleotides 1161, 1163. Referring to FIGS. 7d and 7e, additional target polynucleotide 1160, 1162 have been introduced to region 1154. The amount of probe molecules 1160, 1162 respectively associated with target polynucleotides 1161, 1163 increases in each of FIGS. 7d and 7e as compared to FIG. 7c.

The associating portion of one or both probe molecules may comprise a modified nucleic acid sequence that exhibits a stronger association with the respective target polynucleotides than would a DNA sequence having the same length. For example, the associating portion may comprise a peptide nucleic acid (PNA) sequence that is at least partially complementary to a target polynucleotide to be determined. As discussed in an article by Ray and Norden, The Faseb Journal, vol. 14, June 2000, pages 1041-1060, which article is incorporated herein by reference in its entirety, a duplex comprising a PNA sequence and a DNA sequence exhibits a higher melting temperature than the corresponding duplex comprising two DNA sequences.

Probe molecules comprising PNA sequences may provide more sensitive and selective determination of target polynucleotides than probe molecules comprising DNA sequences. For example, if a second polynucleotide complementary to target polynucleotide 1161 is present within region 1154, the second polynucleotide may compete with polynucleotide 1168 of probe molecule 1160 to form duplexes with target polynucleotide 1161. This competition may relatively reduce the amount of probe molecule 1160 that dissociates from the electrode and associates with target polynucleotide 1161. The relative reduction in dissociation may relatively reduce the change in the electrochemical signal that would otherwise be observed upon introduction of the target polynucleotide 161.

Because PNA sequences may exhibit a stronger association with the target polynucleotide than would a DNA sequence, a PNA sequence will compete more effectively for target polynucleotide present in the detection region 1154. Thus, in the presence of a second complementary polynucleotide, a greater fraction of PNA-comprising probe molecules may associate with a target polynucleotide than of DNA-comprising probe molecules.

Microfluidic Device Fabrication

Microfluidic devices comprising electrode 214 typically include a first substrate and, optionally, a second substrate. Suitable substrates include, e.g., silicon, glass, quartz, polymers, and combinations thereof. The substrates may be planar and may be rigid or flexible. Each substrate typically comprises opposed first and second surfaces.

The first surfaces of one or both of the substrates may be provided with structures, such as one or more of grooves, chambers, channels, and the like, that will define a microfluidic network when the first surfaces of the two substrates are mated with one another. In some embodiments, networks are formed using photolithography and etching to form a pattern preferably including one or more of grooves, chambers, and the like in the first surface of at least one of the substrates. Upon mating the respective first surfaces of the first and second substrates, a microfluidic network comprising at least an electrochemical detection chamber is defined therebetween. In other embodiments, injection molding is used to prepare the substrate.

The microfluidic network includes a detection region as discussed above. An electrode is formed, e.g., by screen printing a flowable mixture of conductive carbon particles. The electrode typically has an area of about 2 mm$^2$ or less, about 1 mm$^2$ or less, or about 0.5 mm$^2$ or less. One or both of a reference electrode and a counter electrode may be positioned in the detection region. One or more electrical leads are fabricated to connect the electrodes to external portions of the device. The electrical leads may be fabricated using photolithography. The sample electrode and, if present, the reference electrode are preferably positioned such that the surfaces of each electrode will be in liquid communication with material present in the electrochemical detection chamber.

At least one probe molecule is associated with the sample electrode surface, such as by reversibly binding the probe molecule to the sample electrode surface. The manufacture of the device may exclude associating, such as by binding, compounds comprising polynucleotide sequences of at least 8 bases in length with the sample electrode surface. At least one electrochemically active probe molecule may be associated with the reference electrode surface, if present. The characteristics of the probe molecule associated with the reference electrode surface are preferably identical with those of the probe molecule associated with the sample electrode surface.

Preferred devices comprise a sufficient amount of probe molecule associated with the sample electrode surface to provide at least about 10 million probe molecules within the detection chamber if all of the probe molecule were to dissociate from the electrode. For example, an exemplary detection chamber has a volume of 1 microliter, an electrode surface of 4000 square microns, and the surface density of probe molecule of 80 attomoles per square mm.

An exemplary electrode, whether sample or reference, comprises carbon. An exemplary method for forming the electrode surface comprises providing a preferably flowable mixture comprising carbon and, preferably, a polymer. Preferred mixtures may be referred to as carbon based inks, such as may be obtained from DuPont Corp. The mixture may also include the probe molecule. Microfabrication techniques including screen printing may be used to deposit the mixture within the electrochemical detection chamber. The probe molecule may also be associated with the electrode surface by forming the electrode surface and contacting the electrode surface with a mixture comprising the probe molecule. An exemplary mixture includes an organic solvent comprising the probe molecule. Probe molecule from the mixture associates, such as by reversible binding, with the electrode surface. The step of associating the probe molecule may be performed prior to, after, or in combination with mating the first and second substrates. Essentially all or all of liquid may be removed from the detection region after fabrication. The electrode may be dried.

The association of the probe molecule with the electrode surface is performed such that (a) a first amount of the probe molecule remains associated with the electrode surface when a liquid comprising a first amount of double stranded polynucleotide is introduced to the electrochemical detection chamber and (b) a second, different amount of the probe molecule remains associated with the electrode surface when a liquid comprising a second, different amount double stranded polynucleotide is introduced to the electrochemical detection chamber. Preferably, the amount of probe molecule that remains associated with the electrode surface is inversely related to the amount double stranded polynucleotide present within the electrochemical detection chamber. For example, if the association of the probe molecule with double stranded polynucleotides is greater than the association of the probe molecule with the electrode surface, more of the probe molecule will become dissociated and remain dissociated from the electrode surface when the double stranded polynucleotide is present than when the double stranded polynucleotide is not present in the electrochemical detection chamber.

An electrochemical activity of the probe molecule when associated with the electrode surface is different from and preferably greater than an electrochemical activity of the probe molecule when not associated with the electrode surface, for example when the probe molecule associates with a double stranded polynucleotide as by intercalation. Upon manufacture of the device, a user may obtain a first electrochemical signal preferably indicative of an amount of electrochemically active probe molecule associated with the sample electrode surface by, for example, applying an electrical potential to the electrode surface and determining a current through a circuit comprising the electrode. The current preferably results from an oxidation or reduction of the probe molecule and not from an oxidation or reduction of the target polynucleotide. Obtaining the first electrochemical signal may comprise the preferably prior introduction of a liquid comprising a known amount of target polynucleotide to the electrochemical detection chamber. The first liquid be free of any of the target polynucleotide. The liquid may be free of the target polynucleotide in double stranded form.

The first electrochemical signal may be obtained from the reference electrode surface if the device was provided with the reference electrode. Because both the same probe molecule is preferably associated with both the sample and reference electrode surfaces, a first electrochemical signal obtained from the reference electrode is indicative of a response that would be obtained from the sample electrode.

A user may introduce to the electrochemical detection chamber a preferably liquid sample in which the amount of a target polynucleotide is to be determined. Preferably, target polynucleotide, if present in the liquid, is hybridized with a second polynucleotide sufficiently complementary to the target polynucleotide to hybridize therewith. If the target polynucleotide and a second, complementary polynucleotide are in single stranded form, the liquid may be subjected to an annealing step, such as by cooling the liquid, to allow hybridization of the target polynucleotide and second complementary polynucleotide.

In the presence of the double stranded polynucleotide, at least some of the probe molecule preferably dissociates from the sample electrode surface and associates with the double stranded polynucleotide. Because the association with the double stranded polynucleotide is preferably stronger than with the electrode surface, the amount of probe molecule associated with the electrode surface decreases. A second electrochemical signal indicative of the amount of electrochemically active probe molecule bound to the electrode surface may be obtained by applying an electrical potential to the electrode surface. A difference between the first and second electrochemical signals is indicative of the presence of the double stranded polynucleotide.

In some embodiments, the microfluidic device includes (a) a sample electrochemical detection chamber and, (b) a reference electrochemical detection chamber. The sample electrochemical detection chamber is spaced apart from the reference electrochemical detection chamber so that different liquids may be simultaneously present within the respective chambers. The device may be configured to introduce a reference sample to the reference electrochemical detection chamber and a sample to the sample electrochemical detection chamber. The reference sample may be identical to the sample with the exception that the reference sample is not subjected to amplification. The device may be manufactured using the same techniques as those described elsewhere herein.

Electrodes associated with one or more probe molecules, whether or not fabricated as part of a network or device, may be sealed within an enclosure, e.g., an enclosure suitable for enclosing the electrochemical detection region (and typically a microfluidic device including the detection region) as for storage and/or shipment to a consumer. The enclosure may be hermetic to limit or prevent evaporation of liquids present in the device. The enclosure may be flexible, e.g., a flexible foil or polymer sack or pouch. The enclosure may be more rigid, e.g. a box. More than one device or detection region may be enclosed within a given enclosure.

EXAMPLES

Microfluidic Device Fabrication

Figure 8:
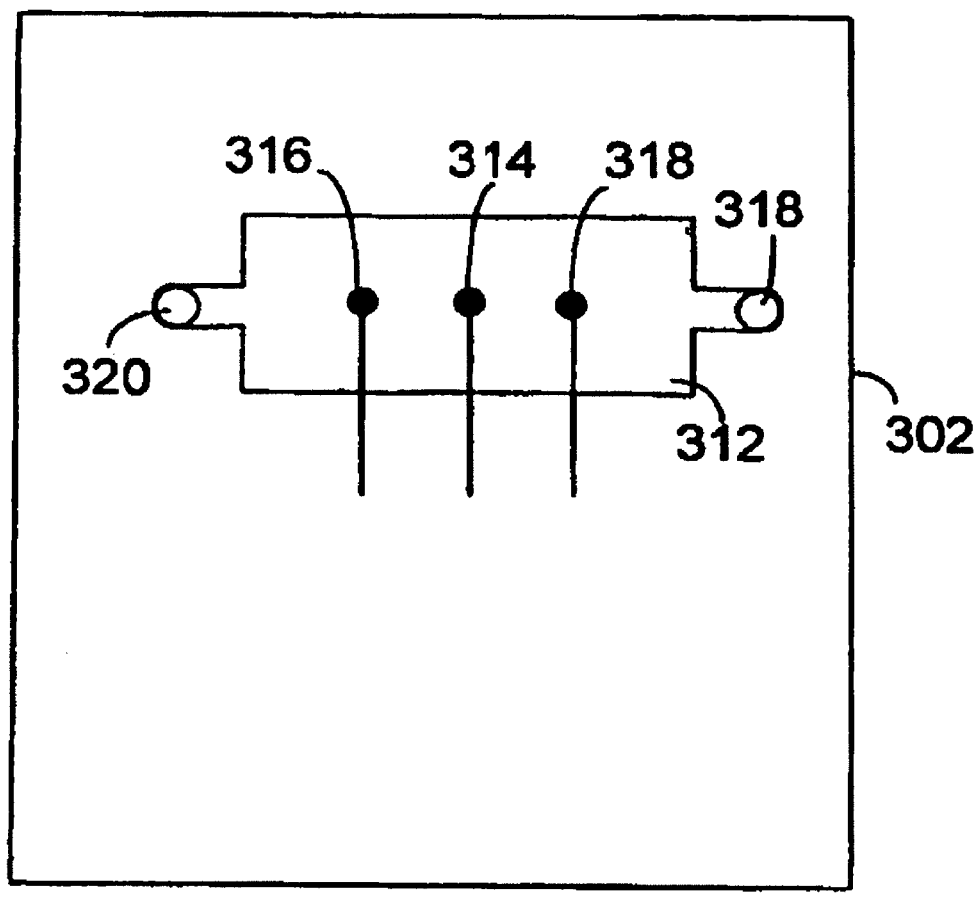
FIG. 8 shows a microfluidic device including an electrode with probe molecules.

Referring to FIG. 8, a microfluidic device 300 includes substrate 302 having a first layer that defines a detection region 312, a working electrode 314, a reference electrode 316, and a third electrode 318. Substrate 302 includes a second, laminated layer that seals detection region 312. An input port 318 allowed the introduction of material to detection region 312 and an output port 320 allowed material to be removed from detection region 312. The volume of detection region 312 was about 1 microliter. During operation of device 300, third electrode 318 was not used.

The first layer of substrate 302 was prepared by injection molding a cyclic olefin polymer (Ticona Topas 5013). A 0.002 inch diameter drill bit was used to form three cavities extending from the outer surface of substrate 302 part way to detection region 312. Two cavities were located toward the ends of the region 312 and one directly in the middle of the region. A 42-gauge needle was used to form a hole extending from the detection region 312 to the each cavity. The size of each hole was just larger than the diameter (100 micron) of a Pd wire to be used for forming a contact to each electrode. A Pd wire (100 micron diameter and 2.5 cm long) was fed through each hole and the wires were folded across the back of substrate 302.

The wire was folded such that about 1 cm of wire extended from the portion of substrate 302 corresponding to detection region 312. About 10 nanoliters of UV glue was applied to the outside of each hole from the bottom side of substrate 302. The UV glue was cured by exposure to UV light for 20 sec. About 500 nanoliters of UV glue was applied over the cured glue and itself cured.

From the detection region side of substrate 302, a razor blade was used to cut each wire just below the surface of the detection region. Uncured UV glue was removed from the detection region using an alcohol swab.

A carbon electrode was formed from the remaining portion of the middle Pd wire by applying a small amount of conductive carbon ink (Dupont #62B) to the wire. Because the wire was cut below the surface of the channel, a small crater resulted above and around the surface of the electrode. Ink was applied so that it filled this depression so that the surface of the ink was flush with the surface of the detection region. The ink was cured with heat by placing the chip under the UV curing lamp for 30 sec. A cotton swab wetted with isopropanol was used to remove excess ink.

A layer of ABI Prism®. well tape was applied over the first layer of substrate 302 to seal detection region 312. The two layers of substrate 302 were fed through a laminating device equipped with revolving heated rollers set at a temperature was set at 110° C. and a feed speed of 5 seconds. Excess lamina beyond the edge of the chip was trimmed using a razor blade.

Probe molecule was bound to working electrode 314 by introducing a 100 micromolar aqueous solution of doxorubicin (DOX) to detection region 312. The solution was allowed to sit for 5 minutes during which time DOX adsorbed onto the working electrode. The detection region was rinsed with about 10 microliters of water. In certain cases, liquid was removed from detection region 312 prior to use. In other cases, detection region 312 remained filled with a liquid, such as water or buffer, prior to use.

Electrochemical Detection of a Double Stranded Polynucleotide

A microfluidic device was prepared as described above without adsorbing DOX to the working electrode 314. For determination of the presence of polynucleotides, the electrochemical detection chamber was loaded with DOX by introduction of 1 microliter of DOX in 50 mM phosphate buffer. The detection region was rinsed and residual liquid was removed from inlet and outlet ports 318, 320. Next, a 2 micro liter aliquot of a Herring sperm DNA sample was introduced into the inlet 318. Fluid was drawn from the outlet port until the inlet port was empty of liquid. A square wave voltammetry (SWV) scan was obtained using a Gamry potentiometer (D1) over a potential range of from −100 mV to −1000 mV (against a Ag/AgCl reference electrode). A frequency of 60 Hz with a pulse amplitude of 50 mV and a scan increment of 2 mV was used.

The detection region 312 was then rinsed with 10 microliters of buffer. Residual liquid was removed from the inlet and outlet ports. A 2 microliter aliquot of the same DNA sample was introduced into the inlet 318 and drawn through detection region 320. A SWV scan was recorded (D2). This process was repeated for samples comprising 0, 2, 5, and 20 ng/ul of DNA.

Figure 9:
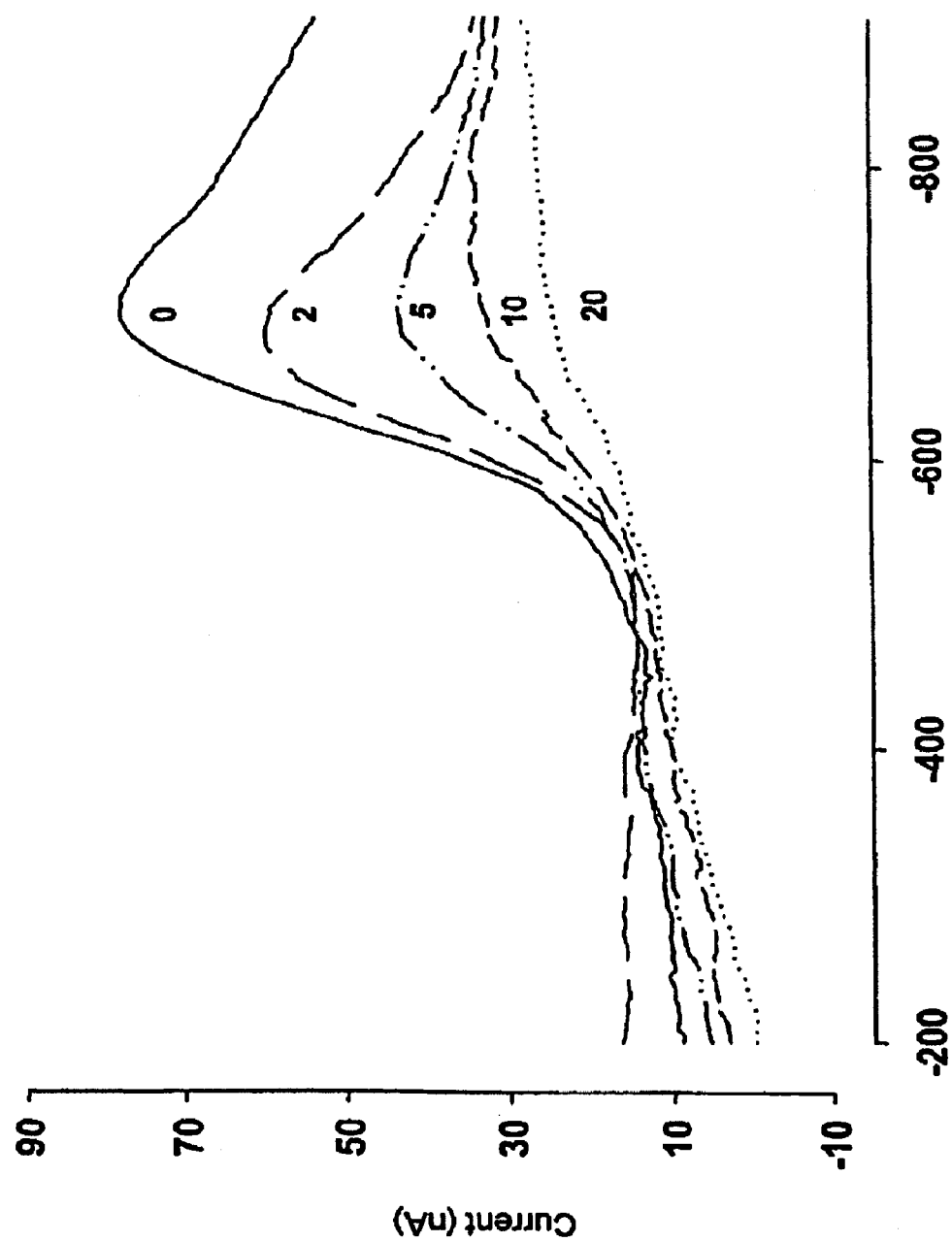
FIG. 9 is a plot of electrochemical signal v. potential obtained using an electrode and probe molecule for solutions having different amounts of target compound.

Referring to FIG. 9, the current observed at an oxidation potential corresponding to DOX (about 700 mV) decreased with increasing DNA concentration.

Detection of Polynucleotides Obtained by Amplification of a Polynucleotide Sample A microfluidic device 300 was prepared as described above and used to obtain electrochemical signals from liquids comprising amplicons prepared by PCR amplification of a Group B *Streptococcus* (GBS) sample.

Amplicons were prepared by adding 5 µl of Group B *Streptococcus* (GBS) PCR reaction mix to each of 15 PCR tubes. The GBS and PCR mixtures were subjected to Taqman PCR in a Light Cycler. After each of a number of cycles, PCR cycling was halted and the fluorescence intensity of the tubes recorded. After recording the fluorescence intensity, one of the PCR tubes was removed from the Light Cycler. This process was repeated until the 15$^{th}$ PCR tube had been removed.

The amplicon samples of the 15 PCR tubes were prepared for electrochemical detection. Each 5 µl amplicon sample was added to a different 250 µl tube. Fifty milimolar (50 mM) phosphate buffer pH 7 was added to each tube and mixed.

The working electrode of the microfluidic device was prepared by introducing 1 µl of a solution of DOX in 50 mM phosphate buffer to the electrochemical detection chamber. Immediately, the chamber was rinsed with 2 µl of the phosphate buffer. Both the inlet and the outlet ports to the detection region were emptied of any residual buffer solution. As a result, the detection region alone remained filled with liquid. Next, a 2 µl aliquot of one of the PCR amplicon samples was introduced into the inlet passage. Fluid was drawn from the outlet portal until the inlet port was empty. A first electrochemical signal was obtained using square wave voltametry (SWV) (S1) using a Gamry potentiometer (R1) over a potential range of −100 mV to −1000 mV (with respect to a Ag/AgCl reference electrode) at a frequency of 60 Hz, a pulse amplitude of 50 mV and a scan increment of 2 mV.

The sensor was then rinsed with 10 µl of buffer. Both the inlet and the outlet ports emptied of residual liquid. Next, a 2 µl aliquot of the same PCR amplicon sample was introduced into the inlet passage. Fluid was drawn from the outlet passage until the inlet passage was empty of liquid. A second electrochemical signal was obtained using SWV (S2). The sensor was rinsed with 10 µl of buffer. Because the probe molecule was not rebound to the working electrode after obtaining the first electrochemical signal, the second electrochemical signal is indicative of a reference response of the working electrode, i.e., a response indicative of the presence of only a small amount of probe molecule associated with the surface of the electrode. The foregoing process was repeated for each amplicon sample.

Figure 10:
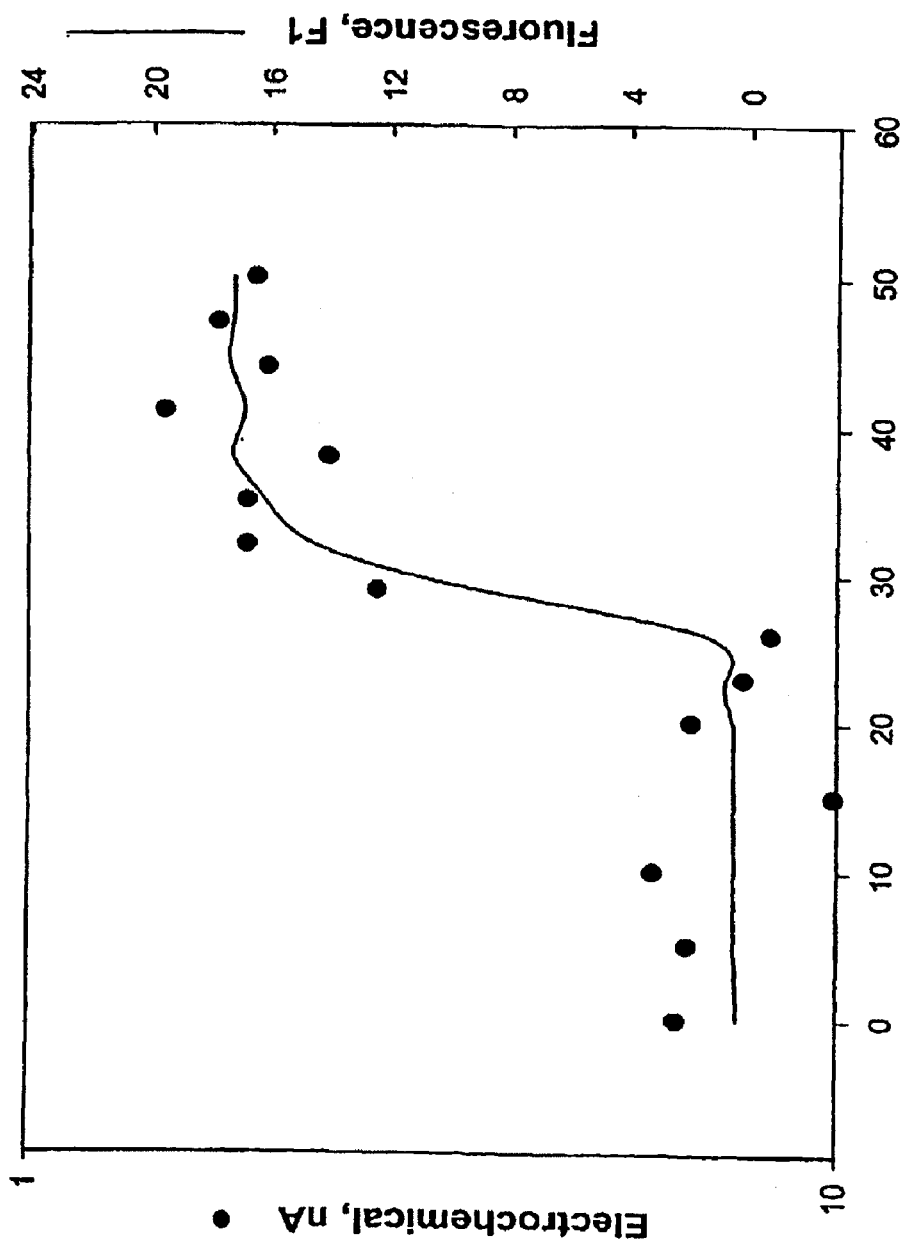
FIG. 10 is a plot of electrochemical signals • and fluorescence signals—obtained from PCR amplicons as a function of the number of amplification cycles.

Referring to FIG. 10, difference between S1 and S2 in nA is plotted for samples from each of the 15 PCR tubes against the number of amplification cycles to which the tube had been subjected. The fluorescence intensity is also plotted against the number of cycles. Each fluorescence intensity is indicative of the amount of GBS amplicon present within the PCR tube. The fluorescence increases as the number of amplification cycles increases. As seen in FIG. 10, the difference between S2 and S1 decreases as the amount of amplicon present in the sample increases. The decrease in the difference of S2 and S1 electrochemical signals indicates that a smaller amount of probe molecule remains associated with the working electrode as the amount of amplicon increases.

Determination of Amplicons Using an Electrode in Communication with a Polynucleotide Amplification Chamber Microfluidic device 300 was used to determine the presence of an amplicon prepared in the presence of electrode 314, e.g., in liquid communication therewith.

A PCR mixture comprising a taqman enzyme and 1000 copies of GBS was prepared. The mixture was divided into two portions. A first portion of the mixture was subjected to heating at 115° C. A second portion of the mixture was not subjected to such heating.

The microfluidic device was prepared by introducing 1 µl of a solution of DOX in 50 mM phosphate buffer to the detection region 312. Immediately, the region 312 was rinsed with 2 µl of the phosphate buffer. Both the inlet and the outlet ports to the chamber were emptied of any residual buffer solution. Next, a 2 µl aliquot of one of the portions of the PCR mixture was introduced into the inlet port. Fluid was drawn from the outlet port until the inlet port was empty of fluid. The inlet and outlet ports of the device were sealed to prevent evaporation.

For each portion of sample, a first electrochemical signal was obtained prior to PCR by scanning a potential applied to the working electrode 314. Then, the contents of the detection region were subjected to 45 denaturing and annealing cycles to prepare amplicons from the initial GBS copies. A second electrochemical signal was obtained.

Figure 11A:
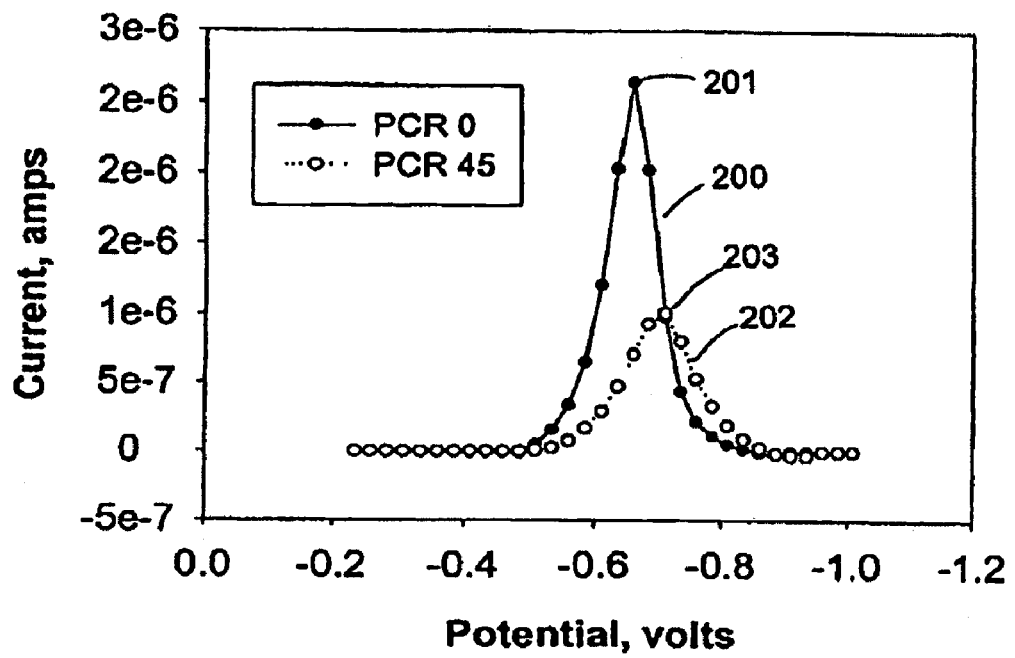
FIG. 11a shows a plot of electrochemical signals for a PCR mixture prior to any amplification cycles and after 45 amplification cycles.
Figure 11B:
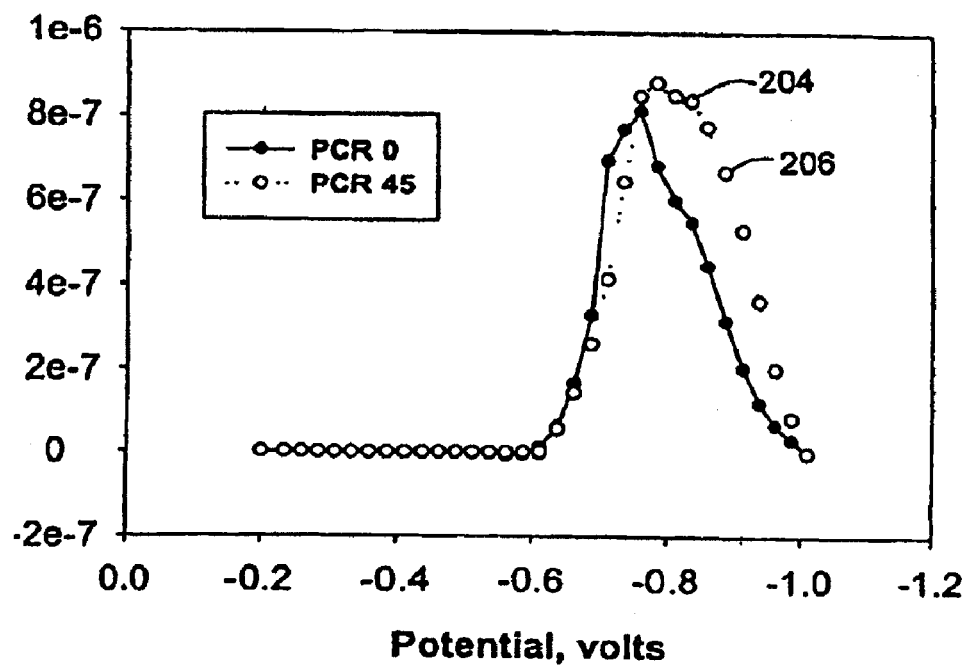
FIG. 11b shows a plot of electrochemical signals for a PCR mixture prior to any amplification cycles and after 45 amplification cycles with the PCR mixture having been subjected to thermal deactivation prior to cycling.
Figure 11C:
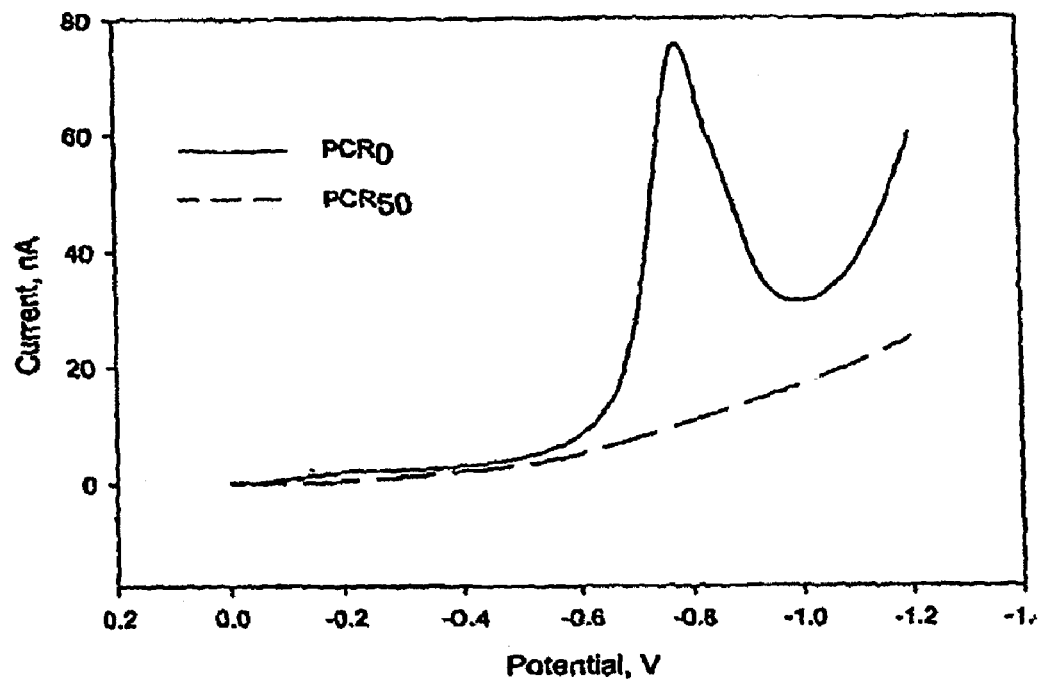
FIG. 11c shows a plot of electrochemical signals for a PCR mixture prior to any amplification cycles and after 50 amplification cycles.
Figure 11D:
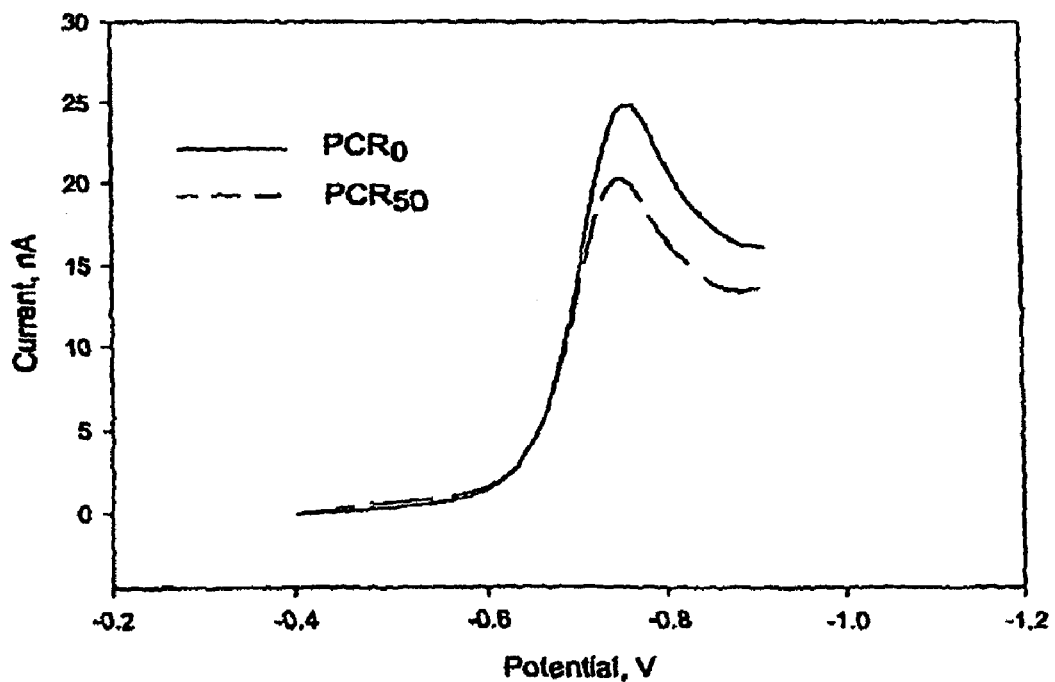
FIG. 11d shows a plot of electrochemical signals for a PCR mixture without a target polynucleotide prior to any amplification cycles and after 50 amplification cycles.

Referring to FIG. 11*b*, a first electrochemical signal 204 and a second electrochemical signal 206 are plotted as a function of potential applied to the first, heated portion of the sample. Referring to FIG. 11*a*, a first electrochemical signal 200 and a second electrochemical signal 202 are plotted as a function of potential applied to the second portion of sample, which had not been subjected to heating at 115° C. A maximum current 201 of the first signal 200 is substantially greater than a maximum current 203 of the second signal 202. The reduction in current is indicative of a reduced amount DOX associated with the working electrode when the second signal 202 was obtained. The amount of DOX associated with the electrode decreases because some DOX dissociates from the working electrode and associates with double-stranded amplicons present in the detection region 312. In contrast, first and second electrochemical signals 204, 206 of the first, heated portion of the sample are not different because of the lack of amplification caused by thermal deactivation of the taqman enzyme. The absence of amplicons in the heated portion of sample and the presence of amplicons in second portion of sample was confirmed via gel electrophoresis.

Referring to 11c electrochemical signals obtained from a carbon electrode comprising adsorbed DOX in the presence of a PCR amplification mixture including a target polynucleotide are shown before and after 50 amplification cycles. Referring to 11d electrochemical signals obtained from a carbon electrode comprising adsorbed DOX in the presence of a PCR amplification mixture missing a target polynucleotide are shown before and after 50 amplification cycles.

The foregoing demonstrates the ability of the present invention to electrochemically determine the presence of an amplicon prepared by PCR amplification in a microfluidic detection chamber comprising an electrode comprising a probe molecule that associates with a double-stranded polynucleotide resulting from the amplification.

Polynucleotide Detection without Modifying the Polynucleotide Concentration

Microfluidic device 300 was used to determine the presence of a polynucleotide without modifying the polynucleotide concentration between electrochemical measurements. The device 300 was prepared with DOX as described above. A sample comprising an amount of target polynucleotide was introduced to detection region 312. Ten consecutive SWV signals were obtained from the same solution.

The microfluidic device was prepared for another set of measurements. A reference sample comprising no target polynucleotide was introduced to the detection region. Ten consecutive SWV signals were obtained from the same solution.

Figure 12:
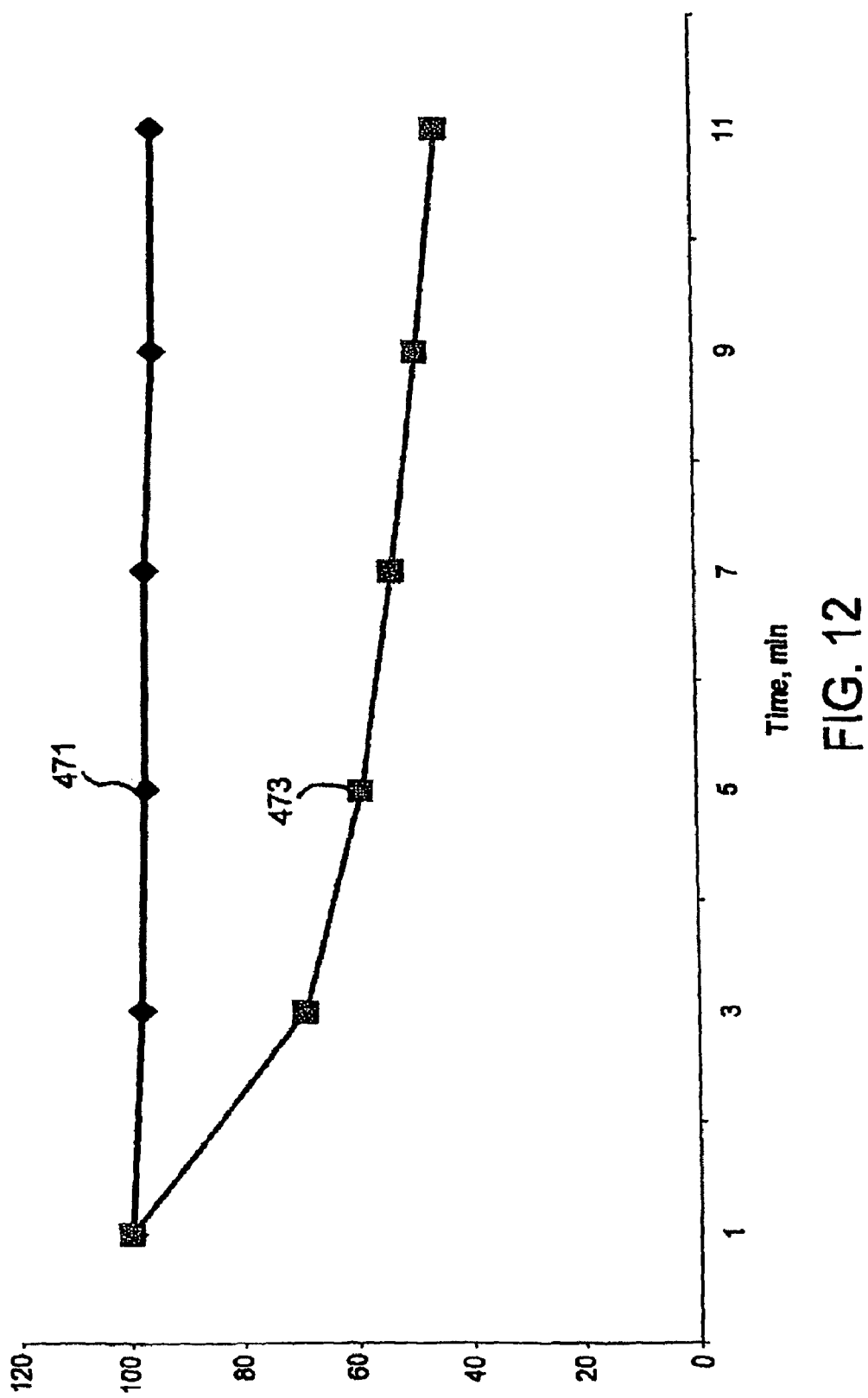
FIG. 12 illustrates sequential electrochemical signals obtained from a reference sample with no target compound and from a sample including a target compound.

Referring to FIG. 12, data points 471 represent the ratio of each reference signal to the initial reference signal at the first iteration. Data points 473 represent the ratio of each sample signal to the initial sample signal at the first iteration. In the presence of the polynucleotide (the sample), the SWV signals decreases at a higher rate than for the SWV in the absence of the polynucleotide (the reference). First and second electrochemical signals may be used to determine the presence or absence of a polynucleotide without modifying the concentration of polynucleotide intermediate the measurements.

Microfluidic device 300 was prepared as above for another determination of the presence of a polynucleotide without modifying the polynucleotide concentration between electrochemical measurements. DOX was adsorbed to the electrode. The same sample comprising the amount of polynucleotide was added to the detection region. Ten pairs of SWV signals followed by chronoamperometry at a fixed potential of −1.3 V for 5 seconds were performed. The sequence was repeated using the reference sample.

Referring to FIG. 13, data points 475 represent the ratio of each reference signal to the initial reference signal at the first iteration with chronoamperometry. Data points 477 represent the ratio of each sample signal to the initial sample signal at the first iteration. With chronoamperometry, the SWV signals of the sample decreases at a higher rate and to a lower value than for the SWV in the absence chronoamperometry (FIG. 12).

Repeated Electrochemical Detection Using an Electrode Associated with a Probe Molecule Repeated electrochemical signals were obtained from a probe molecule without substantial oxidization or reduction thereof. A microfluidic device having a DOX associated electrode was prepared as discussed above. Electrochemical signals were obtained by scanning the electrical potential applied to the electrode without applying a potential sufficient to oxidize or reduce the DOX. The most negative potential was −550 mV. The area under the electrochemical signal response was less than the full response if the scan included potentials of between −550 and −1000 mV. A plurality of measurements of the amount of probe molecule reversibly immobilized with respect to an electrode surface may be performed without electrode regeneration.

While the present invention has been described with reference to one or more preferred embodiments, it should be kept in mind that variations from these are encompassed by the invention, whose scope is defined in the claims below.

What is claimed is:

1. An electrochemical method for detecting a target polynucleotide, comprising:
obtaining a first electrochemical signal, a portion of the first electrochemical signal arising from a first amount of a probe molecule reversibly immobilized on an electrode and not intercalated with the target polynucleotide;
increasing or decreasing an amount of the target polynucleotide in fluid communication with the first amount of the probe molecule, wherein the probe molecule preferentially associates with the target polynucleotide over the electrode;
obtaining a second electrochemical signal, a portion of the second electrochemical signal arising from a second amount of the probe molecule reversibly immobilized on the electrode and not intercalated with the target polynucleotide; and
determining a difference between the first and second electrochemical signals.

2. The electrochemical method of claim 1, wherein the first and second electrochemical signals are obtained using an electrode and the second electrochemical signal is obtained without contacting the electrode with fresh probe molecule intermediate obtaining the first and second electrochemical signals.

3. The electrochemical method of claim 1, wherein the second electrochemical signal is substantially free of a portion arising from an oxidation or reduction of guanine residues, if present, of the target polynucleotide.

4. The electrochemical method of claim 1, wherein, upon increasing or decreasing an amount of target polynucleotide, a portion Δ of the first amount of probe molecule intercalates with the target polynucleotide, the second electrochemical signal being different from the first electrochemical signal by an amount indicative of Δ.

5. The electrochemical method of claim 4, wherein the first and second electrochemical signals are substantially free of an electrochemical signal from the intercalated probe molecule.

6. The electrochemical method of claim 1, wherein the probe molecule is substantially free of polynucleotides having a length of at least 8 bases.

7. The electrochemical method of claim 6, wherein the first and second electrochemical signals arise from an electrochemically active moiety of the probe molecule that is free of purines.

8. The electrochemical method of claim 7, wherein the probe molecule is selected from the group consisting of daunomycin, doxorubicin, methylene blue, toluidine blue O, azure A, azure B, azure C, and thionin.

9. The electrochemical method of claim 7, wherein the probe molecule comprises at least three 6 membered rings.

10. The electrochemical method of claim 7, wherein the probe molecule comprises at least two cyclic groups.

11. The electrochemical method of claim 10, wherein the probe molecule comprises an anthracycline, methylene blue, or derivative thereof.

12. The electrochemical method of claim 7, wherein the probe molecule comprises (a) a polynucleotide having a sequence sufficiently complementary to a sequence of the target polynucleotide to form a duplex therewith and (b) an electrochemically active moiety that is free of purines, the first and second electrochemical signals arising from the electrochemically active moiety.

13. The electrochemical method of claim 12, further comprising detecting a second target polynucleotide, the method comprising:
  obtaining a third electrochemical signal, a portion of the third electrochemical signal arising from a first amount of a second probe molecule reversibly immobilized on an electrode and not intercalated with the target polynucleotide or the second target polynucleotide, the second probe molecule comprising (a) a polynucleotide having a sequence sufficiently complementary to a sequence of the second target polynucleotide to form a duplex therewith and different from the sequence of the polynucleotide of the probe molecule and (b) an electrochemically active moiety that is free of purines;
  increasing or decreasing an amount of the second target polynucleotide in fluid communication with the first amount of the second probe molecule; and
  obtaining a fourth electrochemical signal, a portion of the fourth electrochemical signal arising from a second amount of the second probe molecule reversibly immobilized on an electrode and not intercalated with either the target polynucleotide or the second target polynucleotide.

14. The electrochemical method of claim 13, wherein the second probe molecule is selected from the group consisting of daunomycin, doxorubicin, methylene blue, toluidine blue O, azure A, azure B, azure C, and thionin.

15. The electrochemical method of claim 13, wherein the third and fourth electrochemical signals are obtained using an electrode and the fourth electrochemical signal is obtained without contacting the electrode with fresh second probe molecule intermediate obtaining the third and fourth electrochemical signals.

16. The electrochemical method of claim 13, wherein the fourth electrochemical signal is substantially free of a portion arising from an oxidation or reduction of guanine residues, if present, of the second target polynucleotide.

17. The electrochemical method of claim 13, wherein the second probe molecule is substantially free of polynucleotides having a length of at least 8 bases.

18. The electrochemical method of claim 17, wherein the third and fourth electrochemical signals arise from an electrochemically active moiety of the second probe molecule that is free of purines.

* * * * *